US012807729B2

(12) United States Patent
Schmiege et al.

(10) Patent No.: US 12,807,729 B2
(45) Date of Patent: Nov. 24, 2026

(54) ANTI-HUMAN CYSTINOSIN ANTIBODIES AND METHODS OF USE THEREOF

(71) Applicant: THE BOARD OF REGENTS OF THE UNIVERSITY OF TEXAS SYSTEM, Austin, TX (US)

(72) Inventors: Philip Schmiege, Dallas, TX (US); Linda Donnelly, Dallas, TX (US); Xiaochun Li, Dallas, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 620 days.

(21) Appl. No.: 18/340,608

(22) Filed: Jun. 23, 2023

(65) Prior Publication Data

US 2024/0002528 A1 Jan. 4, 2024

Related U.S. Application Data

(60) Provisional application No. 63/366,972, filed on Jun. 24, 2022.

(51) Int. Cl.
*C07K 16/28* (2006.01)
*G01N 33/53* (2006.01)

(52) U.S. Cl.
CPC ......... *C07K 16/2896* (2013.01); *G01N 33/53* (2013.01); *C07K 2317/14* (2013.01); *C07K 2317/565* (2013.01)

(58) Field of Classification Search
None
See application file for complete search history.

(56) References Cited

U.S. PATENT DOCUMENTS

| | | | | |
|---|---|---|---|---|
| 3,817,837 | A | 6/1974 | Rubenstein et al. | |
| 3,850,752 | A | 11/1974 | Schuurs et al. | |
| 3,939,350 | A | 2/1976 | Kronick et al. | |
| 3,996,345 | A | 12/1976 | Ullman et al. | |
| 4,275,149 | A | 6/1981 | Litman et al. | |
| 4,277,437 | A | 7/1981 | Maggio | |
| 4,366,241 | A | 12/1982 | Tom et al. | |
| 5,196,066 | A | 3/1993 | Kusuda et al. | |
| 5,316,757 | A | 5/1994 | Sherry et al. | |
| 5,342,606 | A | 8/1994 | Sherry et al. | |
| 5,385,893 | A | 1/1995 | Kiefer | |
| 5,428,139 | A | 6/1995 | Kiefer et al. | |
| 5,428,155 | A | 6/1995 | Sherry et al. | |
| 5,462,725 | A | 10/1995 | Kiefer et al. | |
| 5,480,990 | A | 1/1996 | Kiefer et al. | |
| 5,739,294 | A | 4/1998 | Kiefer et al. | |
| 5,750,660 | A | 5/1998 | Kiefer et al. | |
| 5,834,456 | A | 11/1998 | Kiefer et al. | |
| 2010/0111856 | A1 | 5/2010 | Gill et al. | |
| 2020/0207857 | A1* | 7/2020 | Zhu | C07K 16/2827 |
| 2025/0382364 | A1* | 12/2025 | Alteber | C07K 16/2803 |

FOREIGN PATENT DOCUMENTS

WO WO-2013126746 A2 * 8/2013 ............. A61P 35/00

OTHER PUBLICATIONS

De Pascalis et al. "Grafting of abbreviated complementarity determining regions containing specificity determining residues essential for ligand contact to engineer a less immunogenic humanzied monoclonal antibody", Journal of Immunology, 2002. vol. 169, pp. 3076-3084. (Year: 2002).*
Goel et al. Plasticity within the Antigen-Combining Site May Manifest as Molecular Mimicry in the Humoral Immune Response. 1 J. Immunol. 173(12)7358-7367, 2004. (Year: 2004).*
Maccallum et al. "Antibody-antigen interactions: contact analysis and binding site topography", Journal of Molecular Biology, 1996. vol. 262, pp. 732-745. (Year: 1996).*
Mariuzza, R.A. et al. The Structural Basis of Antigen-Antibody Recognition1 Annu. Rev. Biophys. Biphys. Chem. 16:139-159, 1987. (Year: 1987).*
Sailer et al. 'Molecular ensembles make evolution unpredictable.' PNAS 114(45):11938-11943, 2017 (Year: 2017).*
Kahn et al. 'Adjustable Locks and Flexible Keys: Plasticity of Epitope-Paratope Interactions in Germline Antibodies.' J. Immunol. 192:5398-5405, 2014. (Year: 2014).*
Poosarla et al. 'Computational De Novo Design of Antibodies Binding to a Peptide With High Affinity.' Biotech. Bioeng. 114(6): 1331-1342, 2017. (Year: 2017).*
Abu-Remaileh, M., et al. (2017). Lysosomal metabolomics reveals V-ATPase- and mTOR-dependent regulation of amino acid efflux from lysosomes. Science 358, pp. 807-813.
Adams, P.D., et al. (2010). PHENIX: a comprehensive Python-based system for macromolecular structure solution. Acta Crystallogr. D 66, pp. 213-221.
Amick, J., et al. (2020). PQLC2 recruits the C9orf72 complex to lysosomes in response to cationic amino acid starvation. J. Cell Biol. 219, 23 pages.
Andrzejewska, Z., et al. (2016). Cystinosin is a Component of the Vacuolar H+-ATPase-Ragulator-Rag Complex Controlling Mammalian Target of Rapamycin Complex 1 Signaling. J. Am. Soc. Nephrol. 27, 1678-1688.
Bissa, B., et al. (2016). Lysosomal solute carrier transporters gain momentum in research. Clin Pharmacol Ther 100, pp. 431-436. 10.1002/cpt.450.
Bräuer, P., et al. (2019). Structural basis for pH-dependent retrieval of ER proteins from the Golgi by the KDEL receptor. Science 363, pp. 1103-1107.
Briggs, et al., "Synthesis of Functionalized Fluorescent Dyes and Their Coupling to Amines and Amino Acids," J. Chem. Soc., Perkin-Trans. 1 (1997) pp. 1051-1058.
Bröer, S., et al. (2017). Amino acid homeostasis and signalling in mammalian cells and organisms. Biochem. J. 474, 1935-1963.
Bulut, H., et al. (2012). Crystal structures of two solute receptors for L-cystine and L-cysteine, respectively, of the human pathogen Neisseria gonorrhoeae. J. Mol. Biol. 415, 560-572.

(Continued)

*Primary Examiner* — Misook Yu
(74) *Attorney, Agent, or Firm* — Polsinelli PC

(57) ABSTRACT

Provided herein are compositions, methods and kits for targeting Cystinosin protein. These compositions, methods and kits may be used for detecting and quantifying Cystinosin in clinical and non-clinical samples.

20 Claims, 12 Drawing Sheets
(4 of 12 Drawing Sheet(s) Filed in Color)
Specification includes a Sequence Listing.

(56) References Cited

OTHER PUBLICATIONS

Caffrey, M., et al. (2009). Crystallizing membrane proteins using lipidic mesophases. Nat. Protoc. 4, pp. 706-731.
Chen, L.Q., et al. (2010). Sugar transporters for intercellular exchange and nutrition of pathogens. Nature 468, pp. 527-532.
Chen, V.B., et al. (2010). MolProbity: all-atom structure validation for macromolecular crystallography. Acta Crystallogr. D 66, pp. 12-21.
Cherqui, S., et al. (2017). The renal Fanconi syndrome in cystinosis: pathogenic insights and therapeutic perspectives. Nat. Rev. Nephrol. 13, pp. 115-131.
Cherqui, S., et al. (2001). The targeting of cystinosin to the lysosomal membrane requires a tyrosine-based signal and a novel sorting motif. J. Biol. Chem. 276, pp. 13314-13321.
David, D., et al. (2019). Molecular Basis of Cystinosis: Geographic Distribution, Functional Consequences of Mutations in the CTNS Gene, and Potential for Repair. Nephron 141, pp. 133-146.
Emsley, P., et al. (2004). Coot: model-building tools for molecular graphics. Acta Crystallogr. D 60, 2126-2132.
Feng, L., et al. (2015). Structure and function of SemiSWEET and SWEET sugar transporters. Trends Biochem. Sci. 40, pp. 480-486.
Feng, L., et al. (2016). Evolution of Transporters: The Relationship of SWEETs, PQ-loop, and PnuC Transporters. Trends Biochem. Sci. 41, pp. 118-119.
Gahl, W.A. (1987). Disorders of lysosomal membrane transport—cystinosis and Salla disease. Enzyme 38, pp. 154-160.
Gahl, W.A., et al. (1982). Cystine transport is defective in isolated leukocyte lysosomes from patients with cystinosis. Science 217, pp. 1263-1265.
Gahl, W.A., et al. (2002). Cystinosis. N. Engl. J. Med. 347, pp. 111-121.
Goehring, A., et al. (2014). Screening and large-scale expression of membrane proteins in mammalian cells for structural studies. Nat. Protoc. 9, pp. 2574-2585.
Han, L., et al. (2017). Molecular mechanism of substrate recognition and transport by the AtSWEET13 sugar transporter. Proc. Natl Acad. Sci. USA 114, pp. 10089-10094.
Jaehme, M., et al. (2014). Crystal structure of the vitamin B3 transporter PnuC, a full-length SWEET homolog. Nat. Struct. Mol. Biol. 21, 1013-1015.
Jeschke, G., et al. (2006). DeerAnalysis2006—a comprehensive software package for analyzing pulsed ELDOR data. Appl. Magn. Reson. 30, 473-498.
Jezegou, A., et al. (2012). Heptahelical protein PQLC2 is a lysosomal cationic amino acid exporter underlying the action of cysteamine in cystinosis therapy. Proc. Natl Acad. Sci. USA 109, E3434-3443.
Jonas, A.J., et al. (1982). ATP-dependent lysosomal cystine efflux is defective in cystinosis. J. Biol. Chem. 257, pp. 13185-13188.
Jouandin, P., et al. (2022). Lysosomal cystine mobilization shapes the response of TORC1 and tissue growth to fasting. Science 375, eabc4203.
Kabsch, W. (2010). XDS. Acta Crystallogr. D 66, pp. 125-132.
Kalatzis, V., et al. (2001). Cystinosin, the protein defective in cystinosis, is a H(+)-driven lysosomal cystine transporter. EMBO J. 20, pp. 5940-5949.
Kalatzis, V., et al. (2004). Molecular pathogenesis of cystinosis: effect of CTNS mutations on the transport activity and subcellular localization of cystinosin. Hum. Mol. Genet. 13, pp. 1361-1371.
Lee, Y., et al. (2015). Structural basis for the facilitative diffusion mechanism by SemiSWEET transporter. Nat. Commun. 6, pp. 6112.
Leray, X., et al. (2021). Arginine-selective modulation of the lysosomal transporter PQLC2 through a gate-tuning mechanism. Proc. Natl Acad. Sci. USA 118, 10 pages.
Li, X., et al. (2013). Electron counting and beam-induced motion correction enable near-atomic-resolution single- particle cryo-EM. Nat. Methods 10, pp. 584-590.
Li, X., et al. (2016). Clues to the mechanism of cholesterol transfer from the structure of NPC1 middle lumenal domain bound to NPC2. Proc. Natl Acad. Sci. USA 113, pp. 10079-10084.
Liu, B., et al. (2012). LAAT-1 is the lysosomal lysine/arginine transporter that maintains amino acid homeostasis. Science 337, pp. 351-354.
Lobry, T., et al. (2019). Interaction between galectin-3 and cystinosin uncovers a pathogenic role of inflammation in kidney involvement of cystinosis. Kidney Int. 96, pp. 350-362.
Lu, M., et al. (2014). Structural and biochemical analyses of Microcystis aeruginosa O-acetylserine sulfhydrylases reveal a negative feedback regulation of cysteine biosynthesis. Biochim. Biophys. Acta 1844, 308-315.
McCoy, A.J., et al. (2007). Phaser crystallographic software. J. Appl. Crystallogr. 40, 658-674.
McMahon, C., et al. (2018). Yeast surface display platform for rapid discovery of conformationally selective nanobodies. Nat. Struct. Mol. Biol. 25, 289-296.
Otwinowski, Z., et al. (1997). Processing of X-ray diffraction data collected in oscillation mode. Methods Enzymol. 276, 307-326.
Pardon, E., et al. (2014). A general protocol for the generation of Nanobodies for structural biology. Nat. Protoc. 9, 674-693.
Pettersen, E.F., et al. (2004). UCSF Chimera—a visualization system for exploratory research and analysis. J. Comput. Chem. 25, 1605-1612.
Punjani, A., et al. (2017). cryoSPARC: algorithms for rapid unsupervised cryo-EM structure determination. Nat. Methods 14, 290-296.
Rasmussen, S.G., et al. (2011). Structure of a nanobody-stabilized active state of the B(2) adrenoceptor. Nature 469, 175-180.
Rohou, A., et al. (2015). CTFFIND4: Fast and accurate defocus estimation from electron micrographs. J. Struct. Biol. 192, 216-221.
Ruivo, R., et al. (2012). Mechanism of proton/substrate coupling in the heptahelical lysosomal transporter cystinosin. Proc. Natl Acad. Sci. USA 109, E210-217.
Saudek, V. (2012). Cystinosin, MPDU1, SWEETs and KDELR belong to a well-defined protein family with putative function of cargo receptors involved in vesicle trafficking. PLoS ONE 7, e30876.
Schneider, J.A., et al. (1967). Increased cystine in leukocytes from individuals homozygous and heterozygous for cystinosis. Science 157, 1321-1322. 10.1126/science.157.3794.1321.
Sun, Y., et al. (2021). Molecular basis of cholesterol efflux via ABCG subfamily transporters. Proceedings of the National Academy of Sciences of the United States of America 118. 10.1073/pnas.2110483118.
Talaia, G., et al. (2021a). Receptor-like role for PQLC2 amino acid transporter in the lysosomal sensing of cationic amino acids. Proc. Natl Acad. Sci. USA 118, 8 pages.
Talaia, G., et al. (2021b). Receptor-like role for PQLC2 amino acid transporter in the lysosomal sensing of cationic amino acids. Proceedings of the National Academy of Sciences of the United States of America 118. 10.1073/pnas.2014941118.
Tao, Y., et al. (2015). Structure of a eukaryotic SWEET transporter in a homotrimeric complex. Nature 527, pp. 259-263.
Teucher, M., et al. (2018). Improved signal fidelity in 4-pulse DEER with Gaussian pulses. J. Magn. Reson. 296, pp. 103-111.
Town, M., et al. (1998). A novel gene encoding an integral membrane protein is mutated in nephropathic cystinosis. Nat. Genet. 18, 319-324.
Wagner, T., et al.(2019). SPHIRE-crYOLO is a fast and accurate fully automated particle picker for cryo-EM. Commun. Biol. 2, 218.
Wyant, G.A., et al. (2017). mTORC1 Activator SLC38A9 Is Required to Efflux Essential Amino Acids from Lysosomes and Use Protein as a Nutrient. Cell 171, 642-654.e612.
Xu, Y., et al. (2014). Structures of bacterial homologues of SWEET transporters in two distinct conformations. Nature 515, 448-452.
Zhang, J., et al. (2017). Cystinosin, the small GTPase Rab11, and the Rab7 effector RILP regulate intracellular trafficking of the chaperone-mediated autophagy receptor LAMP2A. J. Biol. Chem. 292, pp. 10328-10346.
Zivanov, et al. (2018). New tools for automated high-resolution cryo-EM structure determination in RELION-3. Elife 7, 22 pages.

* cited by examiner

SEQUENCE LISTING

```
Sequence total quantity: 16
SEQ ID NO: 1            moltype = AA  length = 10
FEATURE                 Location/Qualifiers
source                  1..10
                        mol_type = protein
                        organism = synthetic construct
SEQUENCE: 1
GFTFSNYAMS                                                            10

SEQ ID NO: 2            moltype = AA  length = 12
FEATURE                 Location/Qualifiers
source                  1..12
                        mol_type = protein
                        organism = synthetic construct
SEQUENCE: 2
AISGNEGTYT YY                                                         12

SEQ ID NO: 3            moltype = AA  length = 10
FEATURE                 Location/Qualifiers
source                  1..10
                        mol_type = protein
                        organism = synthetic construct
SEQUENCE: 3
ARYGLVGALD                                                            10

SEQ ID NO: 4            moltype = DNA  length = 30
FEATURE                 Location/Qualifiers
source                  1..30
                        mol_type = other DNA
                        organism = synthetic construct
SEQUENCE: 4
ggattcactt tcagtaacta tgccatgtct                                      30

SEQ ID NO: 5            moltype = DNA  length = 36
FEATURE                 Location/Qualifiers
source                  1..36
                        mol_type = other DNA
                        organism = synthetic construct
SEQUENCE: 5
gccattagtg gtaatgaggg tacttacacc tactat                               36

SEQ ID NO: 6            moltype = DNA  length = 30
FEATURE                 Location/Qualifiers
source                  1..30
                        mol_type = other DNA
                        organism = synthetic construct
SEQUENCE: 6
gcaagatatg gactagtggg tgctctggac                                      30

SEQ ID NO: 7            moltype = AA  length = 11
FEATURE                 Location/Qualifiers
source                  1..11
                        mol_type = protein
                        organism = synthetic construct
SEQUENCE: 7
RASQNIDVWL N                                                          11
```

```
SEQ ID NO: 8            moltype = AA  length = 9
FEATURE                 Location/Qualifiers
source                  1..9
                        mol_type = protein
                        organism = synthetic construct
SEQUENCE: 8
IYEASNLHT                                                    9

SEQ ID NO: 9            moltype = AA  length = 10
FEATURE                 Location/Qualifiers
source                  1..10
                        mol_type = protein
                        organism = synthetic construct
SEQUENCE: 9
LQGQDYPFTF                                                   10

SEQ ID NO: 10           moltype = DNA  length = 33
FEATURE                 Location/Qualifiers
source                  1..33
                        mol_type = other DNA
                        organism = synthetic construct
SEQUENCE: 10
cgtgccagtc agaacattga tgtttggtta aac                         33

SEQ ID NO: 11           moltype = DNA  length = 27
FEATURE                 Location/Qualifiers
source                  1..27
                        mol_type = other DNA
                        organism = synthetic construct
SEQUENCE: 11
atctatgagg cttccaactt gcacaca                                27

SEQ ID NO: 12           moltype = DNA  length = 30
FEATURE                 Location/Qualifiers
source                  1..30
                        mol_type = other DNA
                        organism = synthetic construct
SEQUENCE: 12
ctacagggtc aagattatcc attcactttc                             30

SEQ ID NO: 13           moltype = AA  length = 114
FEATURE                 Location/Qualifiers
source                  1..114
                        mol_type = protein
                        organism = synthetic construct
SEQUENCE: 13
EVMLVESGGG LVKPGGSLKL SCAASGFTFS NYAMSWVRQT PEKRLEWVAA ISGNEGTYTY  60
YPDSVRGRFT ISRDNARNNL YLQISSLRSE DTALYYCARY GLVGALDFWG QGAS        114

SEQ ID NO: 14           moltype = AA  length = 103
FEATURE                 Location/Qualifiers
source                  1..103
                        mol_type = protein
                        organism = synthetic construct
SEQUENCE: 14
DIQMNQSPST LSASLGDTIT ITCRASQNID VWLNWYQQKP GDIPKLLIYE ASNLHTGVPS  60
RFSGSGSGTD FTLAISSLQP EDIATYYCLQ GQDYPFTFGS GTK                    103

SEQ ID NO: 15           moltype = DNA  length = 342
FEATURE                 Location/Qualifiers
source                  1..342
                        mol_type = other DNA
                        organism = synthetic construct
SEQUENCE: 15
gaagtgatgc tggtggagtc tgggggaggc ttagtgaagc ctggagggtc cctgaaactc  60
tcctgtgcag cctctggatt cactttcagt aactatgcca tgtcttgggt tcgccagact  120
ccggagaaga ggctggagtg ggtcgcagcc attagtggta atgagggtac ttacacctac  180
tatccagaca gtgtgagggg tcgattcacc atctccagag acaatgccag gaacaacctc  240
tacctgcaaa ttagcagtct gcggtctgaa gacacggcct tgtattattg tgcaagatat  300
ggactagtgg gtgctctgga cttctggggt caaggagcct ca                    342

SEQ ID NO: 16           moltype = DNA  length = 309
FEATURE                 Location/Qualifiers
source                  1..309
                        mol_type = other DNA
                        organism = synthetic construct
SEQUENCE: 16
gacatccaga tgaaccagtc tccttccact ctgtctgcgt ccctcggaga cacaattacc  60
```

-continued

```
atcacttgcc gtgccagtca gaacattgat gtttggttaa actggtacca gcagaaacca  120
ggagatattc ctaagctatt gatctatgag gcttccaact tgcacacagg cgtcccatca  180
aggtttagtg gcagtggatc tggaacagat ttcacattag ccatcagcag tctgcagcct  240
gaagacattg ccacttacta ctgtctacag ggtcaagatt atccattcac tttcggctcg  300
gggacaaag                                                          309
```

ANTI-HUMAN CYSTINOSIN ANTIBODIES AND METHODS OF USE THEREOF

CROSS REFERENCE TO RELATED APPLICATIONS

This application claims the benefit of the U.S. provisional application No. 63/366,972 filed Jun. 24, 2022, the disclosure of which is herein incorporated by reference in its entirety.

ACKNOWLEDGEMENT OF GOVERNMENT SUPPORT

This invention was made with government support under HL020948 awarded by the National Institute of Health (NIH). The government has certain rights in the invention.

SEQUENCE LISTING

This application contains a Sequence Listing that has been submitted in WIPO ST.26 .xml format via EFS-Web and is hereby incorporated by reference in its entirety. The .xml copy is named "106546-763224 UTSD 3961.xml" and is 16 KB in size.

BACKGROUND

1. Field

The present disclosure provides compositions and methods of using a monoclonal antibody targeting Cystinosin.

2. Discussion of Related Art

Cystinosis is a devastating lysosomal storage disease characterized by the abnormal buildup of cysteine, which forms intracellular crystals that gradually damage cells and organs. The accumulation of cysteine occurs in different tissues and organs including kidneys, eyes, muscles, liver, pancreas, and brain. Functional studies have demonstrated that defects in carrier-mediated cysteine transport is a leading cause of cystinosis. Mutations in the CTNS gene that encodes Cystinosin protein in humans can result in cystinosis. The disease is inherited in an autosomal recessive fashion. Cystinosin is a lysosomal seven transmembrane-helix protein that functions as a secondary active transporter for the export of cysteine molecules out of the lysosome. It is a member of the PQ-loop transporter family. Cystinosin dysfunction leads to the accumulation of cysteine inside lysosomes and therefore causes cystinosis.

The specific symptoms and severity of cystinosis vary greatly from one person to another based upon several factors including age of onset and whether the disorder is promptly diagnosed and treated. The disease progression can be greatly slowed by early diagnosis and treatment. Currently, diagnosis involves the measurement of cysteine levels in certain white blood cells and urinary examination. However, these methods of diagnosis are only useful after the appearance of symptoms. There is therefore a need for effective diagnosis before symptom presentation to allow for early intervention and better outcomes.

SUMMARY OF THE INVENTION

In some aspects the current disclosure encompasses an epitope binding agent or conjugate thereof, that specifically binds to Cystinosin, comprising: an immunoglobulin heavy chain variable region ($V_H$) comprising the CDR-H1, CDR-H2, and CDR-H3 of an immunoglobulin heavy chain that comprises at least 80% identity to the amino acid sequence set forth in SEQ ID NO: 1, 2 or 3; and/or an immunoglobulin light chain variable region ($V_L$) comprising the CDR-L1, CDR-L2, and CDR-L3 of an immunoglobulin light chain that comprises at least 80% identity to the amino acid sequence set forth in SEQ ID NO: 7, 8 or 9. In some aspects, the epitope binding agent is the monoclonal antibody Fab3H5 or a derivate, a variant, or fragments thereof In some aspects the current disclosure encompasses an isolated antibody or antigen binding fragment or variant thereof that binds to Cystinosin, wherein the antibody comprises one or more of a heavy chain variable region ($V_H$) comprising: CDR-H1 comprising the amino acid sequence of SEQ ID NO: 1; CDR-H2 comprising the amino acid sequence of SEQ ID NO: 2; CDR-H3 comprising the amino acid sequence of SEQ ID NO: 3; and a light chain variable region ($V_L$) comprising CDR-L1 comprising the amino acid sequence of SEQ ID NO: 7; CDR-L2 comprising the amino acid sequence of SEQ ID NO: 8; and CDR-L3 comprising the amino acid sequence of SEQ ID NO: 9.

In some aspects the epitope binding agent or conjugate thereof or the isolated antibody or antigen binding fragment or variant thereof, comprise a $V_H$ comprising an amino acid sequence comprising at least 70% identity to the amino acid sequence set forth in SEQ ID NO: 13. In some aspects the epitope binding agent or conjugate, or the isolated antibody or antigen binding fragment or variant thereof, comprises a $V_L$ comprising an amino acid sequence at least 70% identity to the amino acid sequence set forth in SEQ ID NO: 14.

In some aspects the epitope binding agent or conjugates disclosed herein is an antibody selected from the group including but not limited to a monoclonal antibody, an IgG, Fv, single chain antibody, nanobody, diabody, scFv, Fab, F(ab')2, and Fab.

In some aspects the current disclosure also encompasses epitope binding agent or conjugates further comprising a detection molecule, for example a fluorescent labels, phosphorescent molecules, chemiluminescent molecules, chromophores, luminescent molecules, photoaffinity molecules, colored particles and/or ligands, such as biotin fluorescent dyes, electro-chemiluminescence dyes, metal-chelate complexes or labels.

In some aspects the current disclosure also encompasses nucleic acid encoding a variable heavy chain ($V_H$) polypeptide, a variable light chain ($V_L$) polypeptide, or both, of an antibody or antigen binding fragment that specifically binds to Cystinosin, wherein the nucleic acid encoding the $V_H$ comprises: nCDR-H1 comprising the nucleic acid acid sequence of SEQ ID NO: 4; nCDR-H2 comprising the nucleic acid sequence of SEQ ID NO: 5; nCDR-H3 comprising the nucleic acid sequence of SEQ ID NO: 6; and wherein the nucleic acid encoding the $V_L$ comprises: nCDR-L1 comprising the nucleic acid sequence of SEQ ID NO: 10; nCDR-L2 comprising the nucleic acid sequence of SEQ ID NO: 11; and nCDR-L3 comprising the nucleic acid sequence of SEQ ID NO: 12.

In some aspects the current disclosure encompasses nucleic acid encoding a variable heavy chain ($V_H$) polypeptide comprising a nucleic acid sequence with at least 60% identity to of SEQ ID NO. 15.

In some aspects the current disclosure encompasses a nucleic acid encoding a variable light chain ($V_H$) polypeptide comprising a nucleic acid sequence with at least 60% identity to of SEQ ID NO. 16. In some aspects the current disclosure also encompasses a host cell comprising the nucleic acid sequences provided herein. In some aspects the current disclosure encompasses a host cell comprising a first nucleic acid encoding the variable heavy chain ($V_H$) polypeptide provided herein; and a second nucleic acid encoding the variable light chain ($V_L$) polypeptide provided herein. In some aspects the host cell is a hybridoma.

In some aspect the current disclosure also encompasses method of isolating the epitope binding agent, the method comprising culturing the host cell under conditions suitable for the cell to express the protein and isolating the epitope binding agent from the cell.

In some aspects the current disclosure provides a method of diagnosing a subject in need thereof with cystinosis, the method comprising contacting the sample with the epitope binding agent; wherein the epitope binding agent specifically binds to Cystinosin to form an epitope binding agent-Cystinosin complex; quantifying a level of the epitope binding agent-Cystinosin complex; and diagnosing the subject with cystinosis if the level of the epitope binding agent-Cystinosin complex is lower than a threshold.

In some aspects the current disclosure also encompasses a method of treating a subject suffering from cystinosis, the method comprising: contacting the sample with the epitope binding agent; wherein the epitope binding agent specifically binds to Cystinosin to form an epitope binding agent-Cystinosin complex; quantifying a level of the epitope binding agent-Cystinosin complex; and diagnosing the subject with cystinosis if the level of the epitope binding agent-Cystinosin complex is lower than a threshold and performing suitable medical intervention to alleviate the condition/symptoms.

In some aspects the current disclosure provides a method of detecting Cystinosin on the surface of a cell, the method comprising: contacting the cell with the epitope binding agent of any one of claims 5-9; wherein the epitope binding agent specifically binds to Cystinosin to form an epitope binding agent-Cystinosin complex; using a detector to determine presence of the epitope binding agent-Cystinosin complex; and quantifying the levels of Cystinosin on the cell. In some exemplary aspects the detector is a microscope linked to a camera.

In some aspects the current disclosure also encompasses kits to carry out the methods provided herein.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Figure 1A:
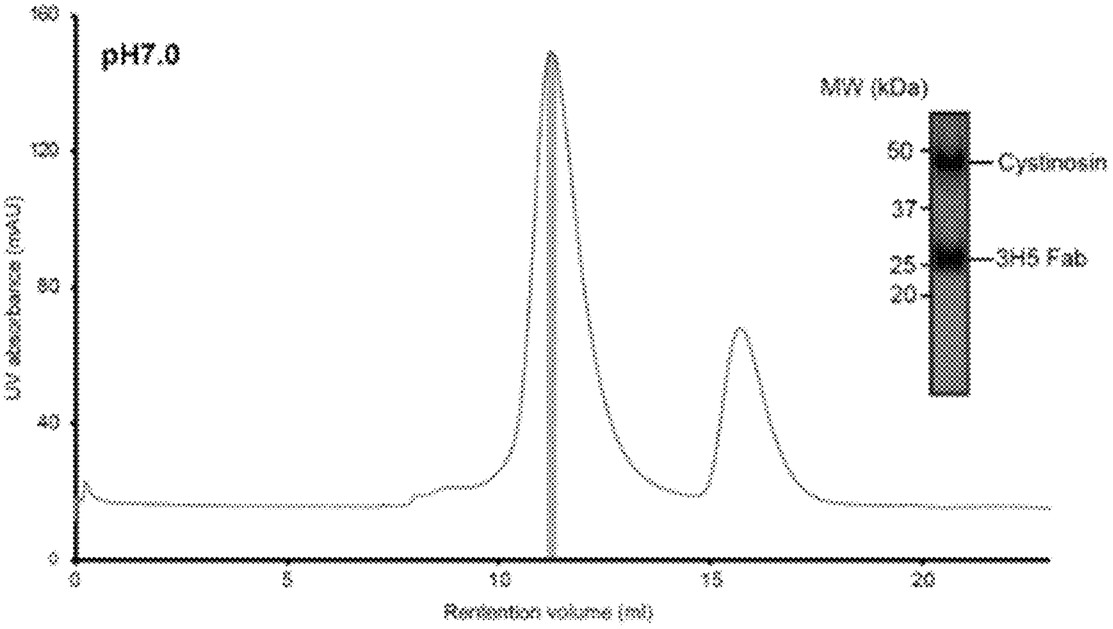
FIG. 1A shows the gel filtration profile for the purified complex comprising Cystinosin bound to Fab3H5. The presence of the complex in the peak fraction was further confirmed on a polyacrylamide gel.

The protein Cystinosin is a Cystine/H+ symporter that mediates export of cysteine, the oxidized dimer of cysteine, from lysosomes. Related to cysteine export, it performs or assists a range of important cellular functions including melanin synthesis, positively regulating of mTORC1 signaling in kidney proximal tubular cells, etc. The protein is encoded by the CTNS gene. Mutations in the gene results in a multisystem genetic disorder called cystinosis. The symptoms and severity of the disease varies greatly based on several factors including age of onset and prompt diagnosis and treatment. The disease can be fatal if left untreated and greatly debilitating even with treatment if the detection is late. Currently, the majority of diagnoses are based on symptom presentation and pre-symptomatic detection is rare though genetic screening is available in some cases.

The present disclosure is based in part on the identification of epitope binding agents comprising antibodies, conjugates and fragments thereof that target the protein Cystinosin. These proteins can greatly assist in advancing functional, structural, and diagnostic analysis of Cystinosin. Accordingly, in some aspects the current disclosure encompasses epitope binding agents and methods of making and using these in clinical and non-clinical settings, compositions comprising these proteins and kits for effective use of these compositions. The detailed description provides some exemplary aspects of the disclosure. The various aspects provided herein can be used in isolation or in combination with described concepts and with other concepts. Other components can be utilized, and changes can be made without departing from the scope. The following description is, therefore, not to be taken in a limiting sense.

I. Terms and Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements. Wherever the terms "comprising" or "including" are used, it should be understood the disclosure also expressly contemplates and encompasses additional aspects "consisting of" the disclosed elements, in which additional elements other than the listed elements are not included.

The term "about" or "approximately," as used herein, can mean within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" can mean an acceptable error range for the particular value, such as 10% of the value modified by the term "about."

The terms "nucleic acid", "nucleic acid molecule", and "polynucleotide" are used interchangeably herein. The terms "nucleic acid encoding . . . ", or "nucleic acid molecule encoding . . . " should be understood as referring to the sequence of nucleotides which encodes a polypeptide.

A polynucleotide described herein may comprise one or more nucleic acids each encoding a polypeptide, all operably linked to (i.e., in a functional relationship with) one or more regulatory sequences, such as a promoter. Such a polynucleotide may alternatively be referred to herein as a "nucleic acid construct" or "construct".

The terms "polypeptide" and "protein," as used interchangeably herein, refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation or any other manipulation or modification, such as conjugation with a labeling component. Also included within the definition are, for example, polypeptides containing one or more analogs of an amino acid (including, for example, unnatural amino acids, etc.), as well as other modifications known in the art. The terms "polypeptide" and "protein" as used herein specifically encompass antibodies.

An amino acid sequence that is "derived from" an amino acid sequence disclosed herein can refer to an amino acid sequence that differs by one or more amino acids compared to the reference amino acid sequence, for example, containing one or more amino acid insertions, deletions, or substitutions as disclosed herein. The terms "derivative," "variant," and "fragment," when used herein with reference to a polypeptide, refers to a polypeptide related to a wild type polypeptide, for example either by amino acid sequence, structure (e.g., secondary and/or tertiary), activity (e.g., enzymatic activity) and/or function. Derivatives, variants and fragments of a polypeptide can comprise one or more amino acid variations (e.g., mutations, insertions, and deletions), truncations, modifications, or combinations thereof compared to a wild type polypeptide.

Within the context of the application a protein is represented by an amino acid sequence and correspondingly a nucleic acid molecule or a polynucleotide represented by a nucleic acid sequence. Identity and similarity between sequences: throughout this application, each time one refers to a specific amino acid sequence SEQ ID NO (take SEQ ID NO: Y as example), one may replace it by: a polypeptide represented by an amino acid sequence comprising a sequence that has at least 60% sequence identity or similarity with amino acid sequence SEQ ID NO: Y. Another preferred level of sequence identity or similarity is 65%. Another preferred level of sequence identity or similarity is 70%. Another preferred level of sequence identity or similarity is 75%. Another preferred level of sequence identity or similarity is 80%. Another preferred level of sequence identity or similarity is 85%. Another preferred level of sequence identity or similarity is 90%. Another preferred level of sequence identity or similarity is 95%. Another preferred level of sequence identity or similarity is 98%. Another preferred level of sequence identity or similarity is 99%.

Each amino acid sequence described herein by virtue of its identity or similarity percentage with a given amino acid sequence respectively has in a further preferred aspect an identity or a similarity of at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% with the given nucleotide or amino acid sequence, respectively. The terms "homology", "sequence identity" and the like are used interchangeably herein. Sequence identity is described herein as a relationship between two or more amino acid (polypeptide or protein) sequences or two or more nucleic acid (polynucleotide) sequences, as determined by comparing the sequences. In a preferred aspect, sequence identity is calculated based on the full length of two given SEQ ID NO's or on a part thereof. Part thereof preferably means at least 50%, 60%, 70%, 80%, 90%, or 100% of both SEQ ID NO's. In the art, "identity" also refers to the degree of sequence relatedness between amino acid or nucleic acid sequences, as the case may be, as determined by the match between strings of such sequences. The degree of sequence identity between two sequences can be determined, for example, by comparing the two sequences using computer programs commonly employed for this purpose, such as global or local alignment algorithms. Non-limiting examples include BLASTp, BLASTn, Clustal W, MAFFT, Clustal Omega, AlignMe, Praline, GAP, BESTFIT, or another suitable method or algorithm. A Needleman and Wunsch global alignment algorithm can be used to align two sequences over their entire length or part thereof (part thereof may mean at least 50%, 60%, 70%, 80%, 90% of the length of the sequence), maximizing the number of matches and minimizes the number of gaps. Default settings can be used and preferred program is Needle for pairwise alignment (in an aspect, EMBOSS Needle 6.6.0.0, gap open penalty 10, gap extent penalty: 0.5, end gap penalty: false, end gap open penalty: 10, end gap extent penalty: 0.5 is used) and MAFFT for multiple sequence alignment (in an aspect, MAFFT v7Default value is: BLOSUM62 [b162], Gap Open: 1.53, Gap extension: 0.123, Order: aligned, Tree rebuilding number: 2, Guide tree output: ON [true], Max iterate: 2, Perform FFTS: none is used).

"Similarity" between two amino acid sequences is determined by comparing the amino acid sequence and its conserved amino acid substitutes of one polypeptide to the sequence of a second polypeptide. Similar algorithms used for determination of sequence identity may be used for determination of sequence similarity. Optionally, in determining the degree of amino acid similarity, the skilled person may also take into account so-called conservative amino acid substitutions. As used herein, "conservative" amino acid substitutions refer to the interchangeability of residues having similar side chains.

For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to Ile or Val; Lys to Arg; Gln or Glu; Met to Leu or Ile; Phe to Met, Leu or Tyr; Ser to Thr; Thr to Ser; Trp to Tyr; Tyr to Trp or Phe; and, Val to Ile or Leu.

The term "epitope binding agent" as used herein refers to any protein, peptide, polypeptide sequence, amino acid sequence, fragments, variants, derivatives, and conjugates thereof that selectively binds Cystinosin and comprise one or more of the disclosed features. For example, in some aspects the "epitope binding agent" may comprise an amino acid sequence comprising any one or more of SEQ ID NOs. 1-3, 7-9, 13, 14. In some aspects, the "epitope binding agent" may be an antibody or antibody fragment.

The term "antibody" herein is used in the broadest sense and encompasses various antibody structures, including but not limited to monoclonal antibodies, polyclonal antibodies, recombinant antibody, single domain antibodies, nanobodies, multispecific antibodies (e.g., bispecific antibodies), and antibody fragments so long as they exhibit the desired antigen-binding activity. The term is further defined and elaborated on in the detailed description.

An "antibody fragment" refers to a molecule other than an intact antibody that comprises a portion of an intact antibody that binds the antigen to which the intact antibody binds. Examples of antibody fragments include, but are not limited to, Fv, Fab, Fab', Fab'-SH, F(ab')2; diabodies; linear antibodies; single-chain antibody molecules (e.g., scFv); and multispecific antibodies formed from antibody fragments. A part or fragment of the antibody may correspond to at least 1%, at least 2%, at least 3%, at least 4%, at least 5%, at least 10%, at least 20%, at least 30%, at least 40% of the length of the disclosed sequence, such as represented by an amino acid sequence with a specific SEQ ID NO, or at least 50%, or at least 60%, or at least 70%, or at least 80%, or at least 90% of the length.

An epitope binding agent "which binds" an antigen of interest, e.g., Cystinosin protein, is one that binds the antigen with sufficient affinity such that the antibody/epitope binding agent is useful as an assay reagent, e.g., as a capture or as a detection antibody/epitope binding agent. Typically, such an antibody/epitope binding agent does not significantly cross-react with other polypeptides. With regard to the binding of a polypeptide to a target molecule, the term "specific binding" or "specifically binds to" or is "specific for" a particular polypeptide or an epitope on a particular polypeptide target means binding that is measurably different from a non-specific interaction. An antibody that "specifically binds" to an antigen or an epitope is a term well understood in the art. A molecule is said to exhibit "specific binding" if for example it reacts more frequently, with more avidity, more rapidly, with greater duration, and/or with greater affinity with a particular target antigen than it does with alternative targets. As an example, an antibody that specifically (or preferentially) binds to an antigen (e.g., Cystinosin) or an antigenic epitope therein is an antibody that binds this target antigen with greater affinity, avidity, more readily, and/or with greater duration than it binds to other antigens or other epitopes in the same antigen. Specific binding can be measured, for example, by determining binding of a target molecule compared to binding of a control molecule, which generally is a molecule of similar structure that does not have binding activity.

As used herein, "binding affinity" refers to the apparent association constant or $K_A$. The $K_A$ is the reciprocal of the dissociation constant ($K_D$).

A "capture antibody," as used herein, refers to an antibody that specifically binds a target molecule, e.g., a form of Cystinosin, in a sample. Under certain conditions, the capture antibody forms a complex with the target molecule such that the antibody-target molecule complex can be separated from the rest of the sample. In certain aspects, such separation may include washing away substances or material in the sample that did not bind the capture antibody. In certain aspects, a capture antibody may be attached to a solid support surface, such as, for example but not limited to, a plate or a bead, e.g., a paramagnetic bead. In some aspects the capture antibody may be conjugated to a detection molecule or label. Examples of detection labels and conjugates are provided herein throughout the application.

A "detection antibody," as used herein, refers to an antibody that specifically binds a target molecule in a sample or in a sample-capture antibody combination material. Under certain conditions, the detection antibody forms a complex with the target molecule or with a target molecule-capture antibody complex. A detection antibody is capable of being detected either directly through a detection molecule or label or dye, which may be amplified, or indirectly, e.g., through use of another antibody that is labeled and that binds the detection antibody. For direct labeling, the detection antibody is typically conjugated to a moiety that is detectable by some means, for example, including but not limited to, biotin, horse radish peroxidase (HRP), fluorescent molecules, radioactive isotopes etc. Other examples of detection labels and conjugates are provided herein.

The term "chimeric" antibody refers to an antibody in which a portion of the heavy and/or light chain is derived from a particular source or species, while the remainder of the heavy and/or light chain is derived from a different source or species.

The term "monoclonal antibody," as used herein, refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies and is not to be construed as requiring production of the antibody by any particular method. For example, the monoclonal antibodies to be used in accordance with the presently disclosed subject matter may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three hyper-variable regions (CDRs). (See, e.g., Kindt et al. Kuby Immunology, 6th ed., W.H. Freeman and Co., page 91 (2007).) A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J Immunol. 150:880-887 (1993); Clarkson et al., Nature 352: 624-628 (1991).

The terms "host cell," "host cell line," and "host cell culture" as used interchangeably herein, refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell but may contain mutations. Mutant progeny that has the same function or biological activity as screened or selected for in the originally transformed cell are included herein. In some aspects the host cell may be a hybridoma.

The term "vector," as used herein, refers to a nucleic acid molecule capable of propagating an-other nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "label" or "detectable label," or "detection molecule" or "detectible molecule" or "conjugate" as used herein, refers to any chemical group or moiety that can be linked to a substance that is to be detected or quantitated, e.g., an antibody. A label is a detectable label that is suitable for the sensitive detection or quantification of a substance. Non-limiting examples of detectable labels include, but are not limited to, luminescent labels, e.g., fluorescent, phosphorescent, chemiluminescent, bioluminescent and electrochemiluminescent labels, radioactive labels, enzymes, particles, magnetic substances, electroactive species and the like. Alternatively, a detectable label may signal its presence by participating in specific binding reactions. Non-limiting examples of such labels include haptens, antibodies, biotin, streptavidin, his-tag, nitrilotriacetic acid, glutathione S-transferase, glutathione and the like. Further specific examples are provided in the current disclosure.

The term "detection means" as used herein, refers to a moiety or technique used to detect the presence of the detectable antibody through signal reporting that is then read out in an assay. Typically, a detection means employ reagents, e.g., a detection agent, that amplify an immobilized label such as the label captured onto a microtiter plate, e.g., avidin, streptavidin-HRP or streptavidin-β-D-galactopyranose.

The term "detecting," is used herein, to include both qualitative and quantitative measurements of a target molecule, e.g., Cystinosin or processed forms thereof. In certain aspects, detect-ing includes identifying the mere presence of the target molecule in a sample as well as deter-mining whether the target molecule is present in the sample at detectable levels.

The term "sample" is used herein to encompass both biological and non-biological samples. In some aspects the sample may be a clinical sample. In some aspects the sample may be a non-clinical sample. In some aspects the sample may be a laboratory sample. The term sample includes both fluid and non-fluid samples. Examples of fluid samples include but are not limited to biological fluids, cell lysates, non-biological fluids like buffers etc. Non-limiting sources of a biological sample for use in the present invention include cells, solid tissue, biopsy, ascites, aspirates, fluidic extracts, blood (including circulating cells), plasma, serum, spinal fluid, lymph fluid, the external sections of the skin, respiratory, intestinal, and genitourinary tracts, tears, saliva, milk, tumors, organs, cell cultures and/or cell culture constituents, for example. Methods for obtaining tissue samples and body fluids from animals (e.g., humans) are well known in the art. Non-fluid samples include but are not limited to cells, tissue samples, samples bound to matrices, strips, solid substrate material or membrane (e.g., plastic, nylon, paper), plates etc.

An "individual" or "subject," as used interchangeably herein, is a mammal. In certain aspects, the individual or subject is a human.

II. Compositions

In some aspects the current disclosure encompasses compositions comprising epitope binding agents, variants, conjugates, and fragments thereof and/or nucleic acid sequences encoding the disclosed epitope binding agents that specifically bind Cystinosin.

Epitope Binding Agent and Antibodies

In some aspects the epitope binding agents provided herein comprise an amino acid sequence that is at least about 80% identical to one or more of SEQ ID NOS. 1-3, 7-9, 13 or 14 provided in Table A. In some aspects the epitope binding agent comprise an amino acid sequence that is at least about 80- about 85%, or about 85% to about 90%, or about 90% to about 95%, or about 95% to about 100% identical to one or more of SEQ ID NOS. 1-3, 7-9, 13 or 14. In some exemplary aspects the epitope binding agents provided herein recognize certain sequence and/or structural features of folded human Cystinosin. In some exemplary aspects the epitope binding agents provided herein recognize structural features of the luminal domain of human Cystinosin.

TABLE A

| SEQ ID NO | Name | Sequence |
|---|---|---|
| 1 | CDR-H1 | GFTFSNYAMS |
| 2 | CDR-H2 | AISGNEGTYTYY |
| 3 | CDR-H3 | ARYGLVGALD |
| 7 | CDR-L1 | RASQNIDVWLN |
| 8 | CDR-L2 | IYEASNLHT |
| 9 | CDR-L3 | LQGQDYPFTF |
| 13 | $V_H$ | EVMLVESGGGLVKPGGSLKLSCAASGFTFSNYAMSWVRQTPEKRLEWVAAISGNEGTYTYYPDSVRGRFTISRDNARNNLYLQISSLRSEDTALYYCARYGLVGALDFWGQGAS |
| 14 | $V_L$ | DIQMNQSPSTLSASLGDTITITCRASQNIDVWLNWYQQKPGDIPKLLIYEASNLHTGVPSRFSGSGSGTDFTLAISSLQPEDIATYYCLQGQDYPFTFGSGTK |

In some exemplary aspects the epitope binding agent is an isolated antibody, or variants, conjugates or fragments thereof that specifically binds Cystinosin. An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (e.g., full-length comprising the Fc and Fab regions) polyclonal or monoclonal antibodies, but also antigen-binding fragments thereof (such as Fab, Fab', F(ab')2, Fv), single-chain antibody (scFv), fusion proteins comprising an antibody portion (e.g., chimeric antigen receptor or CAR), humanized antibodies, chimeric antibodies, diabodies, single domain antibody (e.g., a $V_H$ only antibody such as a nanobody), multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. Furthermore, the term relates to modified and/or altered antibody molecules, as well as to recombinantly or synthetically generated/synthesized antibodies. The term "antibody" also comprises bifunctional antibodies, trifunctional antibodies, chimeric antibodies or antibody-fusion proteins. An antibody encompassed herein may include an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively.

In some aspects the term "antibody" as used herein also comprises recombinant antibodies. The term "recombinant antibody" includes all antibodies that are prepared, expressed, created or isolated by recombinant means. Recombinant antibodies are e.g. antibodies obtained by B-cell PCR, or antibodies isolated from an animal (e.g., a mouse) that is transgenic for human immunoglobulin genes, antibodies expressed using a recombinant expression vector transfected into a host cell, antibodies isolated from a recombinant, combinatorial human antibody library, or antibodies prepared, expressed, created or isolated by any other means that involves splicing of human immunoglobulin gene sequences to other DNA sequences. Recombinant rabbit antibodies as produced by B-cell PCR have variable and constant regions (if present) derived from rabbit germline immunoglobulin sequences. i.e. the direct result of B-cell PCR are the binding relevant fragments of an antibody and the skilled artisan has no problem whatsoever to e.g. construe a full length antibody, a chimeric antibody, or whatever "antibody" that will be desired/required. In some aspects the current disclosure encompasses recombinant antibodies comprising an amino acid sequence provided in any one or more of SEQ ID NOS. 1-3, 7-9, 13 or 14.

An antibody molecule encompassed herein may comprise a heavy chain variable region ($V_H$) and a light chain variable region ($V_L$). The $V_H$ and $V_L$ regions can be further subdivided into regions of hypervariability, also known as "complementarity determining regions" ("CDR"), interspersed with regions that are more conserved, which are known as "framework regions" ("FR"). Each $V_H$ and $V_L$ may be composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the Chothia definition, the AbM definition, and/or the contact definition, all of which are well known in the art. See, e.g., Kabat, E. A., et al. (1991) U.S. Department of Health and Human Services, NIH Publication No. 91-3242; Chothia et al., (1989) Nature 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004).

In some aspects of the current disclosure encompasses antibodies that comprise an amino acid sequence that is at least about 80% identical to one of more of the sequences provided in Table A. In some aspects the isolated antibody provided herein comprises a sequence that is at least 80%, or 81%, or 82%, or 83%, or 84%, or 85%, or 86%, or 87%, or 88%, or 89%, or 90%, or 91%, or 92%, or 93%, or 94%, or 95%, or 96%, or 97%, or 98%, or 99%, or 100% identical to any one or more of SEQ ID NOs. 1-3, 7-9, 13 or 14. In some aspects the antibody herein may comprise a heavy chain variable region that comprises a sequence that has at least 80% identity to the sequence of any one or more of SEQ ID. NOs. 1-3, or 13. In some aspects the antibody herein may comprise a light chain variable region that comprises a sequence that has at least 80% identity to the sequence of any one of SEQ ID. NOs. 7-9, or 14. In some aspects the antibody herein may comprise a heavy chain CDR that has at least 80% identity to the sequence of any one or more of SEQ ID. NOs. 1-3. In some aspects the antibody herein may comprise a light chain CDR that has at least 80% identity to the sequence of any one or more of SEQ ID. NOs. 7-9. In some aspects the antibody herein may comprise a light chain variable region that comprises the sequence of SEQ ID. NO. 14. In some aspects the antibody herein may comprise a heavy chain CDR that has the sequence of SEQ ID. NO. 14. In some aspects the antibody herein may comprise a heavy chain CDR that has the sequence of any one or more of SEQ ID. NOs. 1-3. In some aspects the antibody herein may comprise a light chain CDR that has the sequence of any one or more of SEQ ID. NOs. 7-9.

In some aspects the antibody herein may comprise a heavy chain variable region having the sequence of SEQ ID NO. 13 and a light chain variable region having the sequence of SEQ ID NO. 14.

In an exemplary aspect the antibody provided herein is a monoclonal antibody IgG-3H5 that specifically binds one or more structural epitopes on the luminal domain of folded Cystinosin protein.

In certain aspects, epitope binding agents or antibodies described herein may specifically bind to a corresponding target antigen (e.g., Cystinosin) or an epitope thereof.

In some aspects the antibodies provided herein recognize certain sequence and structural features of folded human Cystinosin. In some aspects the epitope binding agents provided herein recognize structural features of the luminal domain of human Cystinosin.

In certain aspects, antibodies described herein may have a suitable binding affinity for a target antigen (e.g. Cystinosin). In some aspects, an antibody described herein may have a binding affinity ($K_D$) of at least about 1000 nM, at least about 100 nM, at least about 10 nM, at least about 1 nM, at least about 0.1 nM, or lower for an epitope of Cystinosin. In some aspects, an antibody described herein may have a binding affinity ($K_D$) between about 1000 nM to about 0.1 nM (e.g., about 1000 nM, about 750 nM, about 500 nM, about 250 nM, about 100 nM, about 75 nM, about 50 nM, about 25 nM, about 10 nM, about 5 nM, about 1 nM, about 0.75 nM, about 0.5 nM, about 0.25 nM, about 0.1 nM) for Cystinosin. In some aspects, an antibody described herein may have a binding affinity ($K_D$) between about 50 nM to about 40 nM (e.g., about 50 nM, about 49 nM, about 48 nM, about 47 nM, about 46 nM, about 45 nM, about 44 nM, about 43 nM, about 42 nM, about 41 nM, about 40 nM) for Cystinosin protein. In some aspects, an antibody described herein may have a binding affinity ($K_D$) between about 50 nM to about 40 nM (e.g., about 50 nM, about 49 nM, about 48 nM, about 47 nM, about 46 nM, about 45 nM, about 44 nM, about 43 nM, about 42 nM, about 41 nM, about 40 nM) for Cystinosin protein. In some aspects, binding affinity (or binding specificity) can be determined by a variety of methods including equilibrium dialysis, equilibrium binding, gel filtration, ELISA, surface plasmon resonance, and/or spectroscopy (e.g., using a fluorescence assay).

In some aspects, the heavy chain of the antibody disclosed herein may further comprise a heavy chain constant region (CH) or a portion thereof (e.g., CH1, CH2, CH3, or a combination thereof). In some aspects, a heavy chain constant region for use herein may be of any suitable origin, e.g., human, mouse, rat, or rabbit. In some aspects, alternatively or in addition, a light chain of any of the antibodies disclosed herein may further comprise a light chain constant region (CL), which can be any CL known in the art. In some aspects, a CL may be a kappa light chain. In some aspects, a CL may be a lambda light chain. Antibody heavy and light chain constant regions are well known in the art, e.g., those provided in the IMGT database (www.imgt.org) or at www.vbase2.org/vbstat.php., both of which are incorporated by reference herein.

In some aspects, the antibody may be a full-length antibody or an antigen-binding fragment thereof. In some aspects, isolated antibodies herein may be a full-length antibody, which is an IgG molecule. In some aspects, isolated antibodies herein may be a Fab, a (Fab')2, and/or a single-chain antibody. In some aspects, antibodies disclosed herein may be a single chain antibody (scFv). In some aspects, scFv antibody herein may comprise a $V_H$ fragment and a $V_L$ fragment, which may be linked via a linker. In accordance with these aspects, a linker incorporated between the two variable regions herein may be a flexible linker, a rigid linker, a cleavable linker, or any combination thereof. In some aspects, a linker incorporated between the two variable regions herein may be a flexible peptide linker, a rigid peptide linker, a cleavable peptide linker, or any combination thereof. In accordance with these aspects, a peptide linker incorporated between the two variable regions herein may be at least one amino acid. In some aspects, a peptide linker incorporated between the two variable regions herein may be about 1 amino acid to about 50 amino acids (e.g., about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 32, about 34, about 36, about 38, about 40, about 42, about 44, about 46, about 48, about 50). In some aspects, a scFv antibody herein may comprise a $V_H$ fragment and a $V_L$ fragment, which may be linked via a flexible peptide linker. In some exemplary aspects the antibody herein may comprise a heavy chain variable region having the sequence of SEQ ID NO. 13 and/or a light chain variable region having the sequence of SEQ ID NO. 14 and a linker.

In some aspects, a scFv antibody herein may be in the $V_H \rightarrow V_L$ orientation (from N-terminus to C-terminus). In some aspects, a scFv antibody herein may be in the $V_L \rightarrow V_H$ orientation (from N-terminus to C-terminus).

Figure 1B:
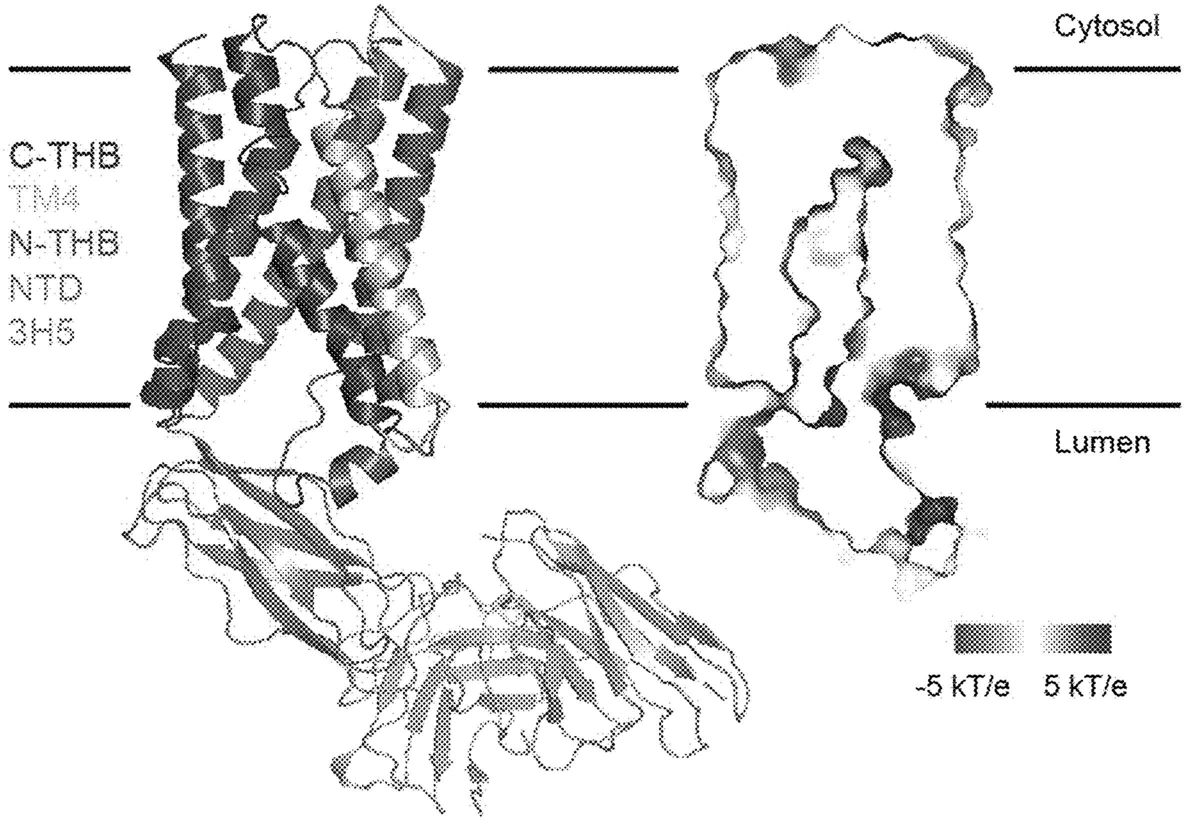
FIG. 1B is a cryo-EM structure of lumen-open Cystinosin bound to Fab3H5, viewed parallel to the membrane. The ribbon representation (left) is colored by structural elements. The slab view (right) is colored by electrostatic potential (red, −5 kT e-1; blue, +5 kT e-1).

In some aspects, antibodies herein can be characterized by identifying an epitope or more than one epitope to which the antigen binds, or "epitope mapping." There are many methods known in the art for mapping and characterizing the location of epitopes on proteins, including, but not limited to, solving the crystal structure of an antibody-antigen complex, cryo-EM, competition assays, gene fragment expression assays, and synthetic peptide-based assays. In some aspects, epitope mapping can be used to determine the sequence, to which an antibody bind. In some particular aspects of the current disclosure the epitope comprises structural features of the luminal domain of Cystinosin. For example, a cryo-EM structure of the antibody Fab3H5 bound to Cystinosin is provided herein (FIGS. 1A and 1B).

In some aspects the current disclosure also encompasses epitope binding agent or antibodies disclosed herein conjugated to a detector molecule (labels, dyes, assay molecules) for example fluorescent labels, phosphorescent molecules, chemiluminescent molecules, chromophores, luminescent molecules, photoaffinity molecules, colored particles and/or ligands, such as biotin fluorescent dyes, electrochemiluminescense dyes, metal-chelate complexes or labels.

Examples of fluorescent dyes are described by Briggs et al "Synthesis of Functionalized Fluorescent Dyes and Their Coupling to Amines and Amino Acids," J. Chem. Soc., Perkin-Trans. 1 (1997) 1051-1058). Examples include a fluorescent label or a dye. A fluorescent label comprises a fluorophore, which is a fluorescent chemical compound that can re-emit light upon light excitation. Examples of fluorescent label include, but are not limited to, xanthene derivatives (e.g., fluorescein, rhodamine, Oregon green, eosin, and Texas red), cyanine derivatives (e.g., cyanine, indocarbocyanine, oxacarbocyanine, thiacarbocyanine, and merocyanine), squaraine derivatives and ring-substituted squaraines (e.g., Seta and Square dyes), squaraine rotaxane derivatives such as SeTau dyes, naphthalene derivatives (e.g., dansyl and prodan derivatives), coumarin derivatives, oxadiazole derivatives (e.g., pyridyloxazole, nitrobenzoxadiazole and benzoxadiazole), anthracene derivatives (e.g., anthraquinones, including DRAQ5, DRAQ7 and CyTRAK Orange), pyrene derivatives such as cascade blue, oxazine derivatives (e.g., Nile red, Nile blue, cresyl violet, and oxazine 170), acridine derivatives (e.g., proflavin, acridine orange, and acridine yellow), arylmethine derivatives (e.g., auramine, crystal violet, and malachite green), and tetrapyrrole derivatives (e.g., porphin, phthalocyanine, and bilirubin). A dye can be a molecule comprising a chromophore, which is responsible for the color of the dye. In some examples, the detectable label can be fluorescein isothiocyanate (FITC), phycoerythrin (PE), biotin, Allophycocyanin (APC) or Alexa Fluor® 488.

Luminescent dyes or labels can be further subcategorized into chemiluminescent and electro-chemiluminescent dyes. The different classes of chemiluminogenic labels include luminol, acridinium compounds, coe-lenterazine and analogues, dioxetanes, systems based on peroxyoxalic acid and their deriva-tives. For immunodiagnostic procedures predominantly acridinium based labels are used (a de-tailed overview is given in Dodeigne C. et al., Talanta 51 (2000) 415-439).

The labels of major relevance used as electrochemiluminescent labels are the Ruthenium- and the Iridium-based electrochemiluminescent complexes, respectively. Electrochemiluminescense (ECL) proved to be very useful in analytical applications as a highly sensitive and selective method. It combines analytical advantages of chemiluminescent analysis (absence of background optical signal) with ease of reaction control by applying electrode potential. In general Ruthenium complexes, especially $[Ru\ (Bpy)^3]^{2+}$ (which releases a photon at ~ 620 nm) regenerating with TPA (Tripropylamine) in liquid phase or liquid-solid interface are used as ECL-labels. Electrochemiluminescent (ECL) assays provide a sensitive and precise measurement of the presence and concentration of an analyte of interest. Such techniques use labels or other reactants that can be induced to luminesce when electrochemically oxidized or reduced in an ap-propriate chemical environment. Such electrochemiluminescence is triggered by a voltage imposed on a working electrode at a particular time and in a particular manner. The light produced by the label is measured and indicates the presence or quantity of the analyte. Recently also Iridium-based ECL-labels have been described.

In one aspect the directly detectable label/molecule is a chemiluminescent or an electrochemiluminescent label. The light produced by the label is measured and directly or indirectly indicates the presence or quantity of the analyte.

Radioactive labels make use of radioisotopes (radionuclides), such as iodine ($^{125}I$, $^{121}I$, $^{124}I$, $^{131}I$), carbon ($^{14}C$, $^{11}C$), sulfur ($^{35}S$), tritium ($^{3}H$), indium ($^{121}In$), Flourine ($^{18}F$), Phosphorus ($^{32}P$), Copper ($^{64}Cu$), Gallium ($^{68}Gn$), Yittrium ($^{86}Y$), Zirconium ($^{89}Zr$), Technetium ($^{99}TC$), Indum ($^{111}In$), Xenon ($^{133}Xe$), Lutetium ($^{177}Lu$), or Astatine ($^{211}At$).

Metal-chelate complexes suitable as labels for imaging purposes are well-known in the art (US 2010/0111856; U.S. Pat. Nos. 5,342,606; 5,428,155; 5,316,757; 5,480,990; 5,462,725; 5,428,139; 5,385,893; 5,739,294; 5,750,660; 5,834,456; Hnatowich et al, J. Immunol. Methods 65 (1983) 147-157; Meares et al, Anal. Biochem. 142 (1984) 68-78; Mir-zadeh et al, Bioconjugate Chem. 1 (1990) 59-65; Meares et al, J. Cancer (1990), Suppl. 10:21-26; Izard et al, Bioconjugate Chem. 3 (1992) 346-350; Nikula et al, Nucl. Med. Biol. 22 (1995) 387-90; Camera et al, Nucl. Med. Biol. 20 (1993) 955-62; Kukis et al, J. Nucl. Med. 39 (1998) 2105-2110; Verel et al., J. Nucl. Med. 44 (2003) 1663-1670; Camera et al, J. Nucl. Med. 21 (1994) 640-646; Ruegg et al, Cancer Res. 50 (1990) 4221-4226; Verel et al, J. Nucl. Med. 44 (2003) 1663-1670; Lee et al, Cancer Res. 61 (2001) 4474-4482; Mitchell, et al, J. Nucl. Med. 44 (2003) 1105-1112; Kobayashi et al Bioconjugate Chem. 10 (1999) 103-111; Miederer et al, J. Nucl. Med. 45 (2004) 129-137; DeNardo et al, Clinical Cancer Research 4 (1998) 2483-90; Blend et al, Cancer Biotherapy & Radiopharmaceuticals 18 (2003) 355-363; Nikula et al J. Nucl. Med. 40 (1999) 166-76; Kobayashi et al, J. Nucl. Med. 39 (1998) 829-36; Mardirossian et al, Nucl. Med. Biol. 20 (1993) 65-74; Roselli et al, Cancer Biotherapy & Radiopharmaceuticals, 14 (1999) 209-20).

In other aspects, derivatization of immunoglobulins by selectively introducing sulfhydryl groups in the Fc region of an immunoglobulin using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region, has also been dis-closed in the literature (O'Shannessy et al., Biotechnol Appl Biochem. 1987 December; 9(6):488-96).

In some aspects the epitope binding agent or antibodies provided herein may also be conjugated to a polynucleotide or a nucleic acid. In some aspects the polynucleotide may be a DNA. In some aspects the polynucleotide may be an RNA. In some aspects the polynucleotide may be a modified DNA or RNA. In some aspects the polynucleotide may comprise a radionuclide.

Polynucleotides and Host Cells

Polynucleotides and vectors can be used to prepare any one of the epitope binding agents including antibodies (e.g., an antibody that binds Cystinosin) using recombinant technology, as exemplified herein. In some aspects the current disclosure also encompasses polynucleotide sequences that comprise a nucleic acid sequence encoding a polypeptide comprising one or more SEQ ID. 1-3, 7-9, 13 or 14 or at least 80% identical to SEQ ID. 1-3, 7-9, 13 or 14. In some aspects the polynucleotide sequence may comprise a nucleic acid sequence that is at least about 70% (e.g., about 75, about 80, about 85%, about 90%, about 95%, about 98% or 100%) identical to the sequence of any one or more of SEQ ID NOs: 4-6, 10-12, 15, or 16.

TABLE B

| SEQ ID NO | Name | Nucleic acid sequence |
|---|---|---|
| 4 | nCDR-H1 | GGATTCACTTTCAGTAACTATGCCATGTCT |
| 5 | nCDR-H2 | GCCATTAGTGGTAATGAGGGTACTTACACCTACTAT |
| 6 | nCDR-H3 | GCAAGATATGGACTAGTGGGTGCTCTGGAC |
| 10 | nCDR-L1 | CGTGCCAGTCAGAACATTGATGTTTGGTTAAAC |
| 11 | nCDR-L2 | ATCTATGAGGCTTCCAACTTGCACACA |
| 12 | nCDR-L3 | CTACAGGGTCAAGATTATCCATTCACTTTC |
| 15 | $nV_H$ | GAAGTGATGCTGGTGGAGTCTGGGGGAGGCTTAGTGAAGCCT<br>GGAGGGTCCCTGAAACTCTCCTGTGCAGCCTCTGGATTCACTT<br>TCAGTAACTATGCCATGTCTTGGGTTCGCCAGACTCCGGAGAA<br>GAGGCTGGAGTGGGTCGCAGCCATTAGTGGTAATGAGGGTACT<br>TACACCTACTATCCAGACAGTGTGAGGGGTCGATTCACCATCTC<br>CAGAGACAATGCCAGGAACAACCTCTACCTGCAAATTAGCAGT<br>CTGCGGTCTGAAGACACGGCCTTGTATTATTGTGCAAGATATG<br>GACTAGTGGGTGCTCTGGACTTCTGGGGTCAAGGAGCCTCA |
| 16 | $nV_L$ | GACATCCAGATGAACCAGTCTCCTTCCACTCTGTCTGCGTCCCT<br>CGGAGACACAATTACCATCACTTGCCGTGCCAGTCAGAACATTG<br>ATGTTTGGTTAAACTGGTACCAGCAGAAACCAGGAGATATTCCT<br>AAGCTATTGATCTATGAGGCTTCCAACTTGCACACAGGCGTCCC<br>ATCAAGGTTTAGTGGCAGTGGATCTGGAACAGATTTCACATTAG<br>CCATCAGCAGTCTGCAGCCTGAAGACATTGCCACTTACTACTGT<br>CTACAGGGTCAAGATTATCCATTCACTTTCGGCTCGGGGACAAA<br>G |

In certain aspects, nucleic acids (i.e., polynucleotides) encoding the heavy and light chain of an antibody as described herein can be cloned into one expression vector, each nucleotide sequence being in operable linkage to a suitable promoter. In some aspects, each of the polynucleotide sequences encoding the heavy chain and light chain may be operably linked to a distinct promoter. In some aspects, polynucleotide sequences encoding the heavy chain and the light chain may be in operable linkage with a single promoter, such that both heavy and light chains are expressed from the same promoter. In some aspects, when necessary, an internal ribosomal entry site (IRES) can be inserted be-tween the heavy chain and light chain encoding sequences.

In some aspects, genetically engineered antibodies such as single-chain antibodies can be produced via, e.g., conventional recombinant technology or any methods known in the art. In some aspects, polynucleotide encoding a monoclonal antibodies specific to a target antigen (e.g. Cystinosin) can be readily isolated and sequenced using conventional procedures (e.g., by using oligonucleotide probes that are capable of binding specifically to genes encoding the heavy and light chains of the monoclonal antibodies). Once isolated, the polynucleotide sequence can be placed into one or more expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. In some aspects the polynucleotide can be modified, for example, by substituting the coding sequence for human heavy and light chain constant domains in place of the homologous murine sequences, or by covalently joining to the immunoglobulin coding sequence all or part of the coding sequence for a non-immunoglobulin polypeptide. In some aspects, genetically engineered antibodies, such as chimeric or hybrid antibodies; can be prepared that have the binding specificity of a target antigen. In some particular aspects, the current disclosure also encompasses hybridomas producing the epitope binding agents or antibodies described herein. In some exemplary aspects the current disclosure encompasses a hybridoma producing the IgG-3H5 monoclonal antibody that specifically binds to Cystinosin. In some aspects the current disclosure encompasses a host cell comprising a polypeptide at least 80% identical to any one or more of SEQ ID NOS. 1-3, 7-9, 13 or 14. In some aspects the current disclosure encompasses a host cell comprising a nucleic acid sequence that is at least about 60% (e.g., about 60%, about 65%, about 70%, about 75%, about 80%, about 85%, about 90%, about 95%, about 98%, about 100%) identical to the sequence of any one or more of SEQ ID NOs: 4-6, 10-12, 15, or 16.

In some aspects, a single-chain antibody herein can be prepared via recombinant technology by linking a polynucleotide sequence coding for a heavy chain variable region and a nucleotide sequence coding for a light chain variable region. In some aspects, a linker may be incorporated between the two variable regions. In some aspects, techniques described to produce single chain antibodies can be adapted to produce a phage or yeast scFv library and scFv clones specific to Cystinosin.

In some aspects, one or more vectors (e.g., expression vectors) having nucleic acids encoding any of the epitope binding agents or antibodies or fragments and variants described herein can be introduced into suitable host cells for producing the antibodies (for example a vector comprising a nucleic acid sequence encoding a polypeptide at least 80% similar to any one or more of SEQ ID NOS. 1-3, 7-9, 13 or 14). In some aspects the current disclosure encompasses vectors comprising a nucleic acid sequence that is at least about 60% (e.g., about 60%, about 65%, about 70%, about 75%, about 80%, about 85%, about 90%, about 95%, about 98%, about 100%) identical to the sequence of any one or more of SEQ ID NOs: 4-6, 10-12, 15, or 16. In some aspects, host cells can be cultured under suitable conditions for expression of the epitope binding agent, or variants thereof. In some aspects, epitope binding agents can be recovered from the cultured cells (e.g., from the cells or the culture supernatant) via a conventional method, e.g., affinity purification. In some aspects, polypeptide chains of the antibody herein can be incubated under suitable conditions for a suitable period of time allowing for production of the antibody or functional epitope binding agents.

In certain aspects, standard molecular biology techniques can be used to prepare the recombinant expression vector, transfect the host cells, select for transformants, culture the host cells, and recover the epitope binding agent or antibodies from the culture medium. In some aspects, some antibodies can be isolated by affinity chromatography with a Protein A or Protein G coupled matrix.

In some aspects the current disclosure also encompasses compositions that comprise one or more of these epitope binding agents or antibodies for in vivo diagnostic use. In some aspects these diagnostic compositions are used in conjunction with in vivo imaging techniques. In some exemplary aspects, epitope binding agents or antibodies may be coupled to dyes, fluorophores or radiolabels as provided above, but for in vivo imaging of Cystinosin. Epitope binding agents of the invention may be administered neat to detect levels of Cystinosin in vivo in accordance with the present disclosure. More commonly, however, they are administered in the context of acceptable compositions, that contains effective amounts of one or more antibodies together with one or more other ingredients known to those skilled in the art for formulating compositions for in vivo use.

Additional ingredients useful in preparing these in vivo diagnostics in accordance with the present disclosure include, for example, carriers (e.g., in liquid or solid form), flavoring agents, lubricants, solubilizers, suspending agents, fillers, glidants, compression aids, binders, tablet-disintegrating agents, encapsulating materials, emulsifiers, buffers, preservatives, sweeteners, thickening agents, coloring agents, viscosity regulators, stabilizers or osmo-regulators, or combinations thereof.

Liquid diagnostic compositions preferably contain one or more monoclonal antibodies of the invention and one or more liquid carriers to form solutions, suspensions, emulsions, syrups, or pressurized compositions. An acceptable liquid carriers include, for example water, organic solvents, acceptable oils or fat, or combinations thereof. The liquid carrier can contain other suitable additives such as solubilizers, emulsifiers, buffers, preservatives, sweeteners, flavoring agents, suspending agents, thickening agents, colors, viscosity regulators, stabilizers or osmo-regulators, or combinations thereof. If the liquid formulation is intended for pediatric use, it is generally desirable to avoid inclusion of alcohol.

Examples of liquid carriers suitable for oral or parenteral administration include water (preferably containing additives such as cellulose derivatives such as sodium carboxymethyl cellulose), alcohols or their derivatives (including monohydric alcohols or polyhydric alcohols such as glycols) or oils (e.g., fractionated coconut oil and *arachis* oil). For parenteral administration the carrier can also be an oily ester such as ethyl oleate and isopropyl myristate. The liquid carrier for pressurized compositions can be halogenated hydrocarbons or other acceptable propellant.

III. Methods of Use

Cystinosin is a lysosomal seven-transmembrane protein that functions as a secondary active transporter for the export of cysteine molecules out of the lysosome. Mutations in this protein lead to the rare genetic disorder known as cystinosis. This disorder is characterized by a lack of transport of the natural substrate cysteine. In some aspects the epitope binding agent provided herein recognize structural features of the luminal domain of Cystinosin allowing the antibody to recognize and bind the protein in cells. The ability of the antibody provided herein to recognize and bind Cystinosin in a structurally specific way, may be utilized in methods for detection of folded protein in in vitro or ex vivo samples and in vivo with suitable administration means.

Assaying for the expression of Cystinosin protein is intended to include detection, qualitative or quantitative measurement or estimation of the level of Cystinosin protein or variants or fragments thereof in a sample either directly (e.g., by determining or estimating absolute protein level) or relatively (e.g., by comparing to Cystinosin protein level in a second sample or standard). Cystinosin polypeptide expression level in the sample can be measured or estimated and compared to a standard Cystinosin protein level, the standard being determined from a second biological sample healthy individual or being determined by averaging levels from a population of samples that are not diseased. As will be appreciated in the art, once the "standard" Cystinosin polypeptide level is known, it can be used repeatedly as a standard for comparison.

Samples as used herein may vary depending on the application. For example, it may be a biological sample or a non-biological sample. The term non-biological sample may include synthetic peptides, buffers, non-clinical fluids, artificial antigen bound surfaces etc. The term "biological sample" includes any biological specimen obtained from an individual. Suitable samples for use in the present invention include, without limitation, tissue samples, biopsy, cells, sections, whole blood, plasma, serum, saliva, urine, stool (i.e., feces), tears, and any other bodily fluid. One skilled in the art will appreciate that samples can be diluted prior to the analysis of marker levels. The sample may be a fluid sample, a solid sample or a sample bound to a solid surface like matrices, beads, strips, solid substrate material or membrane (e.g., plastic, nylon, paper), plates etc.

The clinical and non-clinical methods of use provided herein share some common principles for detection, qualitative or quantitative measurement. In general, the epitope binding agent or antibody provided herein is contacted with a sample comprising Cystinosin to form a complex that is either directly detectible due to the presence of a detectible molecule or can be indirectly detected by a detection antibody. Methods to conduct these assays are well established in the art.

In some aspects the current disclosure encompasses methods of using the epitope binding agent and antibodies provided herein to detect and/or assay Cystinosin protein (for clinical and non-clinical purposes) in a sample using methods known to those of skill in the art, including immunoassays, such as immunohistochemistry (IHC), enzyme linked immunosorbent assay (ELISA), fluorescence-activated cell sorting (FACS), immunohistochemistry (IHC), immunoprecipitation, radioimmunoassays, electrochemiluminescence-based detection assays, magnetic immunoassays, lateral flow assays, and related techniques and Western blotting. Additional suitable immunoassays for detecting the target antigen in a sample will be apparent to those of skill in the art. Methods for performing these assays are known in the art.

In some aspects, anti-Cystinosin epitope binding agent described herein can carry a detectable molecule. When radioactive labels are used, currently available counting procedures known in the art may be utilized to identify and quantitate the specific binding of the epitope binding agent to Cystinosin (e.g., human Cystinosin). In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with the epitope binding agent, for example anti-Cystinosin antibody or antigen-binding protein of fragments thereof under conditions that allow for the formation of a complex between the epitope binding agent and Cystinosin. Any complexes formed between the epitope binding agent and Cystinosin may be detected and compared in the sample and the control. In light of the specific binding of the antibodies or antigen-binding fragments thereof described herein for Cystinosin, the antibodies or antigen-binding fragments thereof can be used to specifically detect for example Cystinosin expression, e.g., in whole cells, cell lysates, membrane extracts, on cell membranes, or in cytoplasm. The epitope binding agent or conjugates thereof described herein can also be used to purify Cystinosin via immunoaffinity purification.

The steps of various useful immunodetection methods have been described in the scientific literature, such as, e.g., Doolittle M H and Ben-Zeev O, Methods Mol Biol. 1999; 109:215-37; Gulbis B and Galand P, Hum Pathol. 1993 December; 24(12):1271-85; and De Jager R et al., Semin Nucl Med. 1993 April; 23(2):165-79, each incorporated herein by reference.

In general, the immunobinding methods include obtaining a sample, e.g. a sample suspected of comprising Cystinosin, and contacting the sample with a first epitope binding agent, for example anti-Cystinosin antibody in accordance with the present invention under conditions effective to allow the formation of immunocomplexes. Contacting the chosen biological sample with the antibody under effective conditions and for a period of time sufficient to allow the formation of immune complexes (primary immune complexes) generally comprises adding the antibody composition to the sample and incubating the mixture for a period of time sufficient for the antibodies to form immune complexes with, i.e., to specifically bind to, any Cystinosin present. After this time, the sample-antibody composition, such as a tissue section, ELISA plate, dot blot or western blot, will generally be washed to remove any non-specifically bound antibody species, allowing only those antibodies specifically bound within the primary immune complexes to be detected In general, the detection of immunocomplex formation is well known in the art and may be achieved through the application of numerous approaches. These methods are generally based upon the detection of a label or marker, such as for example any of radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. In some aspects, a secondary binding agent, such as a second antibody and/or a biotin/avidin ligand binding arrangement, may be used in accordance with methodologies known in the art.

In some aspects, the first epitope binding agent for example antibody that becomes bound within the primary immune complexes may be detected by means of a second binding agent that has binding affinity for the antibody. In these cases, the second binding agent may be linked to a detectable label or detectable molecules provided herein. In some aspects, the second binding agent is an antibody, which may thus be termed a "secondary" antibody. The primary immune complexes for example Cystinosin-epitope binding agent complex are contacted with the labeled, secondary binding agent, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding agent, such as an antibody, that has binding affinity for the primary immune complex is used to form secondary immune complexes, as described above. After washing, the secondary immune complexes are contacted with a third binding agent or antibody that has binding affinity for the second antibody, again under effective conditions and for a period of time sufficient to allow the formation of immune complexes (tertiary immune complexes). The third ligand or antibody is linked to a detectable molecule, allowing detection of the tertiary immune complexes thus formed. This system may provide for signal amplification if this is desired. Thus in some aspects, any of the primary (epitope binding agent of the current disclosure), secondary or tertiary antibodies may be conjugated to a detectible molecule (examples of which are provided herein).

In some aspects, a biotinylated antibody or epitope binding agent is used to detect the target antigen(s), and a second step antibody is then used to detect the biotin attached to the complexed antibody. In that method the sample to be tested is first incubated in a solution comprising the first step antibody. If the target antigen is present, some of the antibody specifically binds to the antigen to form a biotinylated antibody/antigen complex. The anti-body/antigen complex is then amplified by incubation in successive solutions of streptavidin (or avidin) and biotinylated DNA, and/or complementary biotinylated DNA, with each step adding additional biotin sites to the antibody/antigen complex. The amplification steps are repeated until a suitable level of amplification is achieved, at which point the sample is incubated in a solution comprising the second step antibody against biotin. This second step antibody is labeled, as for example with an enzyme that can be used to detect the presence of the antibody/antigen complex by histoenzymology using a chromogen substrate. With suitable amplification, a conjugate can be produced that is macroscopically visible.

In one aspect, immunohistochemistry (IHC) is used for immunological detection. Using IHC, detection of Cystinosin in a sample can be achieved by targeting a sample with a epitope binding agent, e.g., an anti-Cystinosin antibody or antigen-binding fragment thereof. The binding agent can be linked, either directly or indirectly to a detectable label or can be detected by another binding agent that is linked, either directly or indirectly to a detectable label. In one aspect, 3,3'-diaminobenzidine (DAB) is used in the HIC assay to detect the primary antibody bound to Cystinosin. In one aspect, the concentration of the anti-Cystinosin antibody or antigen-binding fragment thereof in the IHC assay is about 1 μg/ml to about 50 μg/ml. In one aspect, the concentration of the anti-Cystinosin antibody or antigen-binding fragment thereof in the IHC assay is about 1 μg/ml to about 20 μg/ml. In one aspect, the concentration of the anti-Cystinosin antibody or antigen-binding fragment thereof in the IHC assay is about 10 μg/ml.

IHC can be performed on cells, cell pellets, tissues, preparations from blood, plasma, serum, or lymph fluid, etc. In some aspects, the samples are fixed samples. In some aspects, the samples are paraffin embedded samples. In some aspects, the samples are formalin fixed and paraffin embedded samples.

In one aspect, flow cytometry is used for immunological detection. Thus, for example, the number of antibodies bound per cell (ABC) can be assessed using flow cytometry.

In some aspects, the current disclosure also encompasses methods of using the compositions provided herein for in vivo diagnostics applications. In some aspects the compositions provided herein are used in medical imaging of a subject, in need thereof. In some exemplary aspects the method encompasses administering to a subject an imaging effective amount of an in vivo diagnostic composition, wherein the composition comprises the epitope binding agent coupled to a detectable moiety for example a dye or a radiolabel. The localization and accumulation of the imaging agent is then detected. The localization and accumulation of the imaging agent may be detected by for example radionuclide imaging, radio scintigraphy, nuclear magnetic resonance imaging, computed tomography, positron emission tomography, computerized axial tomography, X-ray or magnetic resonance imaging method.

IV. Kits

The assay methods and compositions of this invention can be provided in the form of a kit. In some aspects, such a kit comprises the epitope binding agent or conjugate thereof thereof provided herein.

In an exemplary aspect the kit comprises the epitope binding agent disclosed herein; a reporter molecule that detects the Cystinosin-antibody (epitope binding agent) complex, suitable reagents and instructions for use.

In some exemplary aspects the current disclosure also encompasses kits for IHC and related applications comprising: the epitope binding agent compositions provided herein, a reporter molecule that detects Cystinosin-antibody complex (epitope binding agent), suitable detection reagents, and instructions for use.

In some exemplary aspects the current disclosure also encompasses diagnostic kits comprising means for obtaining a sample from a subject in need thereof; the epitope binding agent provided herein, a reporter molecule that detects the epitope binding agent complex, reagents and instructions for use.

In some aspects, such a kit is a packaged combination including the basic elements of: a capture antibody comprised of an anti-Cystinosin antibody; a detectable (labeled or unlabeled) antibody that binds to the antibody of interest and instructions on how to perform the assay method using these reagents.

The kit may further comprise a solid support for the capture reagents, which may be provided as a separate element or on which the capture reagents are already immobilized. In some aspect the capture antibody (anti-Cystinosin) may already be immobilized on the solid support for example a plate, matrix, paper strip, plastic strip, beads.

Hence, the capture antibodies in the kit may be immobilized on a solid support, or they may be immobilized on such support that is included with the kit or provided separately from the kit. In some aspects, the capture reagents are coated on or attached to a solid material (for example, a microtiter plate, beads or a comb). The detectable antibodies may be labeled antibodies detected directly or unlabeled antibodies that are detected by labeled antibodies directed against the unlabeled antibodies raised in a different species or targeted to another epitope. Where the label is an enzyme, the kit will ordinarily include substrates and cofactors required by the enzyme; where the label is a fluorophore, a dye precursor that provides the detectable chromophore; and where the label is biotin, an avidin such as avidin, streptavidin, or streptavidin conjugated to HRP or β-galactosidase with MUG.

The kit also typically contains the analyte for example purified intrinsic factor of interest as a standard as well as other additives such as stabilizers, washing and incubation buffers, and the like.

The components of the kit will be provided in predetermined ratios, with the relative amounts of the various reagents suitably varied to provide for concentrations in solution of the reagents that substantially maximize the sensitivity of the assay. Particularly, the reagents may be provided as dry powders, usually lyophilized, including excipients, which on dissolution will provide for a reagent solution having the appropriate concentration for combining with the sample to be tested.

In various embodiments, a kit comprising an antibody as described herein is for use in a method as described herein (e.g., in a method of detecting Cystinosin). In some aspects, the kit further comprises an anti-Cystinosin antibody coated or attached to a comb for use in a method of detecting or quantifying Cystinosin in biological samples.

In some aspects the article of manufacture or kit comprises a container and a label or package insert on or associated with the container. Suitable containers include, for example, bottles, vials, syringes, assay plates, strips, matrices etc. The containers may be formed from a variety of materials such as glass, plastic, paper etc. The kit may further include other materials desirable from a commercial and user standpoint, including other buffers, diluents, filters, needles, and syringes.

A "package insert" is used to refer to instructions customarily included in commercial packages of diagnostic products, that contain information about usage etc.

Instructions included in the kits may be affixed to packaging material or may be included as a package insert. While the instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

As various changes could be made in the above-described cells and methods without departing from the scope of the invention, it is intended that all matter contained in the above description and in the examples given below, shall be interpreted as illustrative and not in a limiting sense.

Examples

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

The publications discussed throughout are provided solely for their disclosure before the filing date of the present application. Nothing herein is to be construed as an admission that the invention is not entitled to antedate such disclosure by virtue of prior invention.

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1. Protein Expression and Purification of Recombinant Human Cystinosin In one aspect the current disclosure encompasses novel antibodies for use in non-clinical, laboratory and clinical settings. An important aspect towards achieving this goal is to purify Cystinosin.

Purification and proper folding of transmembrane proteins can however be challenging. As a first step to successfully purify Cystinosin, full-length human cystinosin-LKG (GenBank: BC032850.2) was cloned into pEG-BacMam with a C-terminal Flag tag. The protein was expressed using baculovirus-mediated transduction of mammalian HEK-293S GnTI$^-$ cells (ATCC no. CRL-3022) grown at 37° C. for 48 hours post transduction. Cells were disrupted by sonication in lysis buffer (20 mM HEPES pH 7.5, 150 mM NaCl, 1 mM PMSF and 5 μg/mL leupeptin). After low-speed centrifugation, the supernatant was incubated with 1% (w/v) n-Dodecyl-b-D-Maltopyranoside (DDM, Anatrace) at 4° C. for 1 hour. The lysate was clarified by another centrifugation, and the resulting supernatant was loaded onto a Flag-M2 affinity column (Sigma-Aldrich). The resin was washed twice with wash buffer containing 20 mM HEPES pH7.5, 150 mM NaCl, and 0.02% DDM. The protein was eluted by wash buffer with 100 μg/mL 3×Flag peptide. The eluate was then concentrated and purified by SEC on a Superdex 200 Increase column (Cytiva). SEC buffer containing 20 mM HEPES pH7.5, 150 mM NaCl, and 0.06% (w/v) Digitonin (ACROS Organics) was used to obtain the apo lumen-open conformation, while SEC buffer containing 20 mM sodium acetate pH 5.0, 150 mM NaCl, and 0.06% (w/v) Digitonin was used to obtain the apo cytosol-open conformation. To prepare cysteine-bound cystinosin, protein samples were purified similarly with minor changes. 100 mM Cystine stock was made in 1 M HCl due to its low solubility in neutral pH conditions. Buffers were supplemented with 1 mM cysteine immediately prior to use, yielding a final pH of ~7.0. Cells were sonicated in lysis buffer containing 20 mM HEPES pH8.5, 150 mM NaCl, and 1 mM cysteine (Alfa Asar). The SEC buffer contained 20 mM HEPES pH8.5, 150 mM NaCl, 1 mM Cystine, and 0.06% Digitonin.

Example 2. Generation of Anti-Human Cystinosin Monoclonal Antibody 3H5

IgG-3H5, a mouse monoclonal anti-human Cystinosin antibody, was prepared by fusion of SP2-mlL6 mouse myeloma cells (ATCC no. CRL-2016) with splenic B lymphocytes obtained from BALB/c mice (n=2) at UT Southwestern with the approval of the Institutional Animal Care and Research Advisory Committee #2017-102391 as previously described. Briefly, mice were immunized with one primary and eight boosts of purified recombinant human Cystinosin reconstituted in amphipols (50 μg) in phosphate buffered saline (PBS) combined with Sigma Adjuvant System. Hybridomas were initially grown in HAT (hypoxanthine-aminopterin-thymidine) medium (DMEM high glucose supplemented with 20% FBS, 10% NCTC 109, and 1% each of HAT, ITS, NEAA, NaPyr, GlutaMAX, and Pen/strep). Hybridomas were created by fusion of splenic B lymphocytes from hyperimmune mice to SP2-mlL6 mouse myeloma cells (CRL-2016). One ELISA-positive, immunoblot-negative, immunoprecipitation-positive clone, designated IgG-3H5, was serial diluted four times. The monoclonal hybridoma was expanded into a roller bottle culture and the culture supernatant purified on a Protein G sepharose column by gravity flow. Hybridoma culture supernatants were screened by ELISA and counter-screened by western blot to select ELISA positive, western blot negative clones. The hybridoma, designated IgG-3H5 (subclass IgG1), was subcloned by serial dilution three times and grown up in roller bottles in HT medium (DMEM high glucose supplemented with 10% FBS, 10% NCTC 109, and 1% each of HT, ITS, NEAA, NaPyr, GlutaMAX, and Pen/strep). IgG-3H5 was then purified from the hybridoma culture supernatant by gravity-flow affinity chromatography on protein G Sepharose 4 Fast Flow columns (Cytiva).

The purified antibody was able to recognize folded human Cystinosin protein by immunoprecipitation. The Fab region was sequenced by RNA extraction (Qaigen), subsequent PCR (Superscript III) with degenerate primers. The resulting PCR sequences were analyzed with the IMGT database to determine complementarity-determining regions. A final PCR (Promega) with designed primers including restriction sites were used to clone possible nucleotide regions for the variable heavy and light regions into a shuttle vector and transfected into Expi293F cells. The supernatant was collected and purified similarly on Protein G sepharose gravity columns. The binding of the recombinant Fab region was consistent with that of the antibody produced by the hybridoma. The following are the amino acid sequences for the heavy and light chain variable regions: Heavy Chain:

```
EVMLVESGGGLVKPGGSLKLSCAASGFTFSNYAMSWVRQTPEKRLEWVA
AISGNEGTYTYYPDSVRGRFTISRDNARNNLYLQISSLRSEDTALYYCA
RYGLVGALDFWGQGAS
and

Light Chain:
DIQMNQSPSTLSASLGDTITITCRASQNIDVWLNWYQQKPGDIPKLLIY
EASNLHTGVPSRFSGSGSGTDFTLAISSLQPEDIATYYCLQGQDYPFTF
GSGTK
```

In order to confirm specificity and conduct structural and functional studies, the 3H5 antibody was further processed. The Fab fragment was generated by Papain cleavage in buffer containing 20 mM HEPES pH7.5, 150 mM NaCl, 10 mM cysteamine hydrochloride, 10 mM β-mercaptoethanol, and 10 mM EDTA. After incubation at 37° C. for 2 hours, the reaction was stopped by adding iodoacetamide to a final concentration of 23 mM and then incubated at room temperature for 20 minutes. The protein mixture was dialyzed overnight in buffer containing 10 mM HEPES pH7.5 and 10 mM NaCl. Fab3H5 was further purified by a Hitrap Q column (Cytiva) and used for cryo-EM studies.

Example 3. Generation of Cystinosin and Anti-Human Cystinosin Antibody Fab3H5 Complex and Cryo-EM Structure Determination To assemble Cystinosin-Fab$^{3H5}$ complex, purified Cystinosin was incubated with Fab$^{3H5}$ at a 1:1.5 molar ratio at 4° C. for 30 minutes. The mixture was then purified by SEC using the aforementioned buffer (FIG. 1A). Peak fractions were collected and concentrated to ~5 mg/ml. The isolated complex was then used for functional and structural studies. In particular the complex was used in Cryo-EM studies.

The Cystinosin-Fab$^{3H5}$ complex samples (~5 mg/ml) were applied to Quantifoil R1.2/1.3 400 mesh Au holey carbon grids (Quantifoil). The grids were then blotted and plunged into liquid ethane for flash freezing using a Vitrobot Mark IV (FEI). The grids were imaged in a 300 kV Titan Krios (FEI) with a Gatan K3 Summit direct electron detector (Gatan). Data were collected at 0.842 or 0.844 Å/pixel. Images were recorded for 5 second exposures in 50 subframes with a total dose of ~60 electrons per Å$^2$.

The images were collected in three sessions corresponding to the sample conditions and corresponding conformations of Cystinosin: apo lumen-open conformation (5258 images from 400 mesh grids); apo cytosol-open conformation (7133 images from 400 mesh grids); cysteine-bound lumen-open conformation (4991 images from 400 mesh grids). Dark subtracted images were first normalized by gain reference. Motion correction was performed using the program MotionCor2. The contrast transfer function (CTF) was estimated using CTFFIND4. Autopicking was performed with crYOLO v1.7.6 using a general model, and a particle threshold of 0.2. About 0.9-1.2 million particles were extracted for each dataset. Subsequent 2D classification, multi-class Ab-Initio modeling, heterogenous 3D refinement, and non-uniform refinement of the best class were performed for all 3 datasets in cryoSPARC v3.1.0. For the two apo conformations, further 3D classification, refinements with and without masks and Baysian polishing were performed in RELION-3.1. The final maps for the apo conformations were then obtained with a final non-uniform refinement in cryoSPARC using the polished particles from RELION-3.1.

Figure 1C:
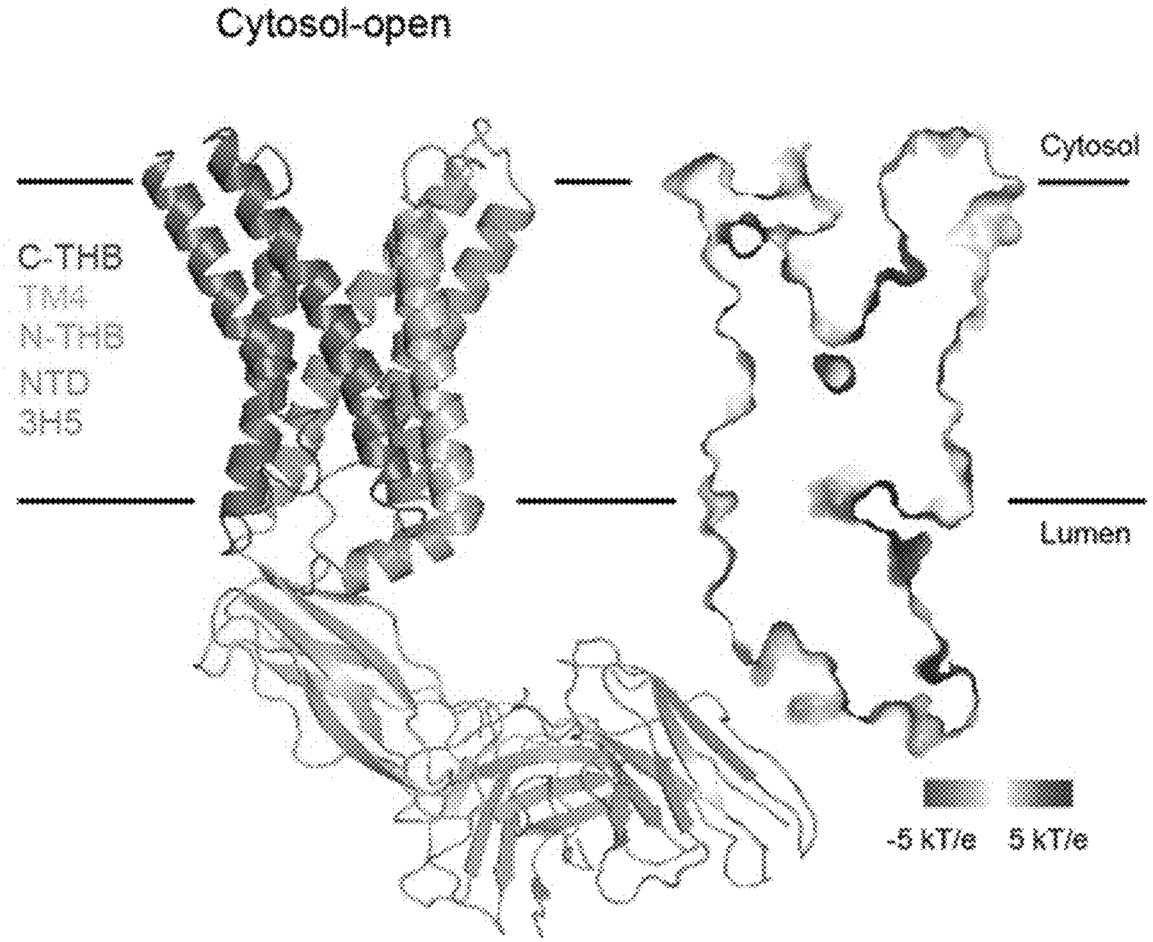
FIG. 1C is a cryo-EM structure of cytosol-open Cystinosin bound to Fab3H5, viewed parallel to the membrane. The ribbon representation (left) is colored by structural elements. The slab view (right) is colored by electrostatic potential (red, −5 kT e-1; blue, +5 kT e-1).
Figure 1D:
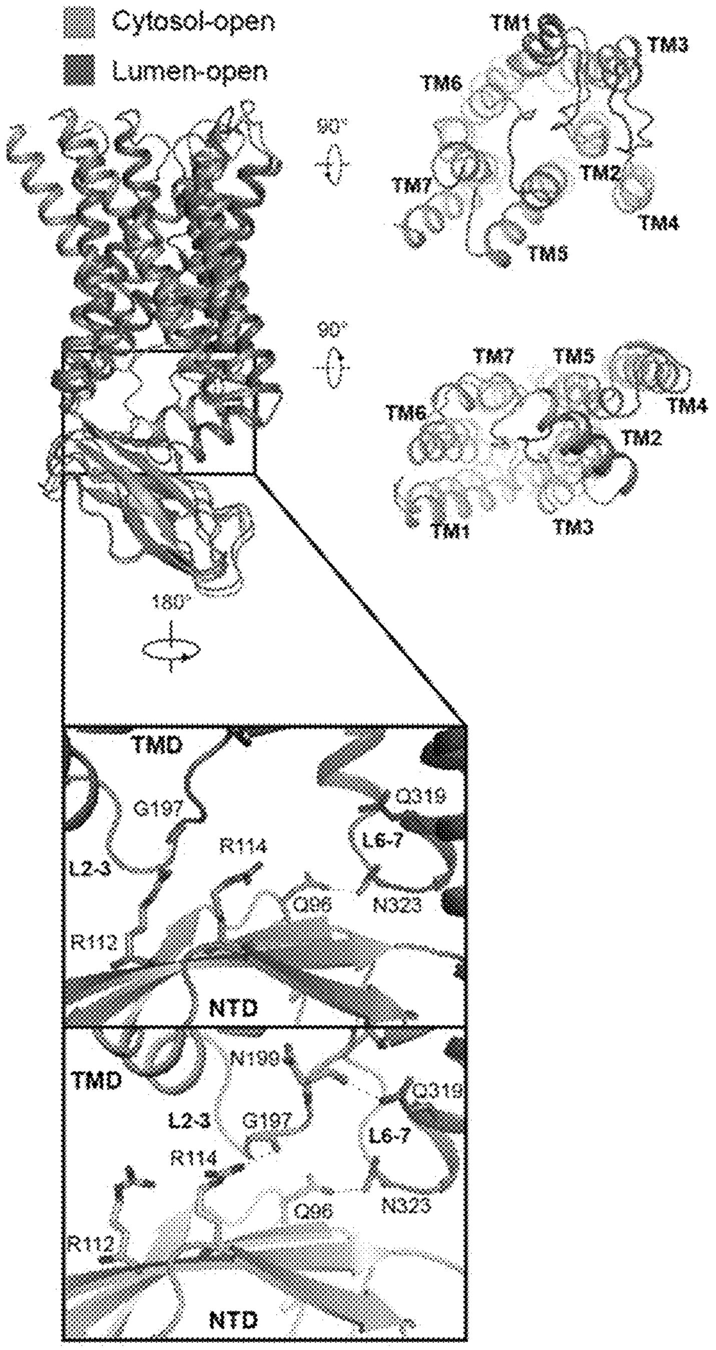
FIG. 1D shows a comparison of the cryo-EM cytosol-open (green) and lumen-open (blue) structures. TM rearrangements are shown from the cytosolic side (top) and the luminal side (bottom). A close-up views of NTD-TMD interactions in the lumen-open (blue) and cytosol-open (green) structures is also provided. Residues involved in NTD-TMD interactions are shown as sticks. The hydrophilic interactions are indicated by gray dashes.

Cryo-EM structures of wild-type (WT) human Cystinosin in complex with Fab3H5 in two conformational states were determined. Cystinosin-Fab3H5 purified at pH 7.5 yielded a lumen-open conformation structure at 3.4 Å resolution (see FIG. 1B) Cystinosin Fab3H5 purified at pH 5.0 yielded a 3.2 Å resolution cytosol-open conformation structure (see FIG. 1C) with pronounced conformational changes in the TMD that resulted in a large central cavity accessible from the cytosolic side.

Cryo-EM structures of wild-type (WT) human Cystinosin in complex with Fab3H5 in two conformational states were determined. Cystinosin-Fab3H5 purified at pH 7.5 yielded a lumen-open conformation structure at 3.4 Å resolution (see FIG. 1B). In contrast, Cystinosin Fab3H5 purified at pH 5.0 yielded a 3.2 Å resolution cytosol-open conformation structure (see FIG. 1C) with pronounced conformational changes in the TMD that resulted in a large central cavity accessible from the cytosolic side.

Figure 2A:
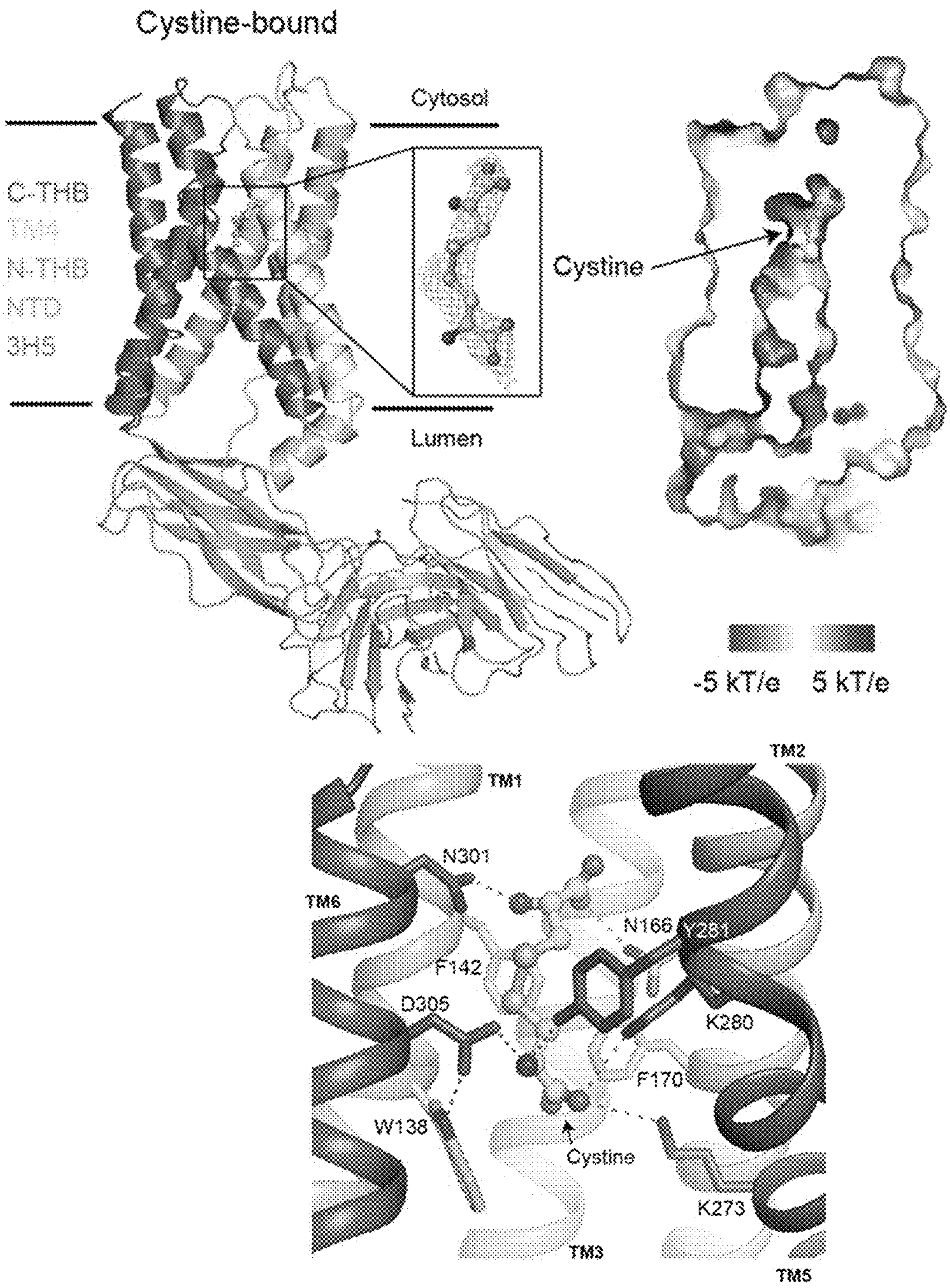
FIG. 2A is Cryo-EM structure of Cystinosin-Fab3H5 bound to cysteine, viewed parallel to the membrane. The ribbon representation (left) is colored by structural elements, with zoomed-in view of cysteine density. The slab view (right) is colored by electrostatic potential (red, −5 kT e-1; blue, +5 kT e-1). A close up of the cysteine-binding pocket shows key residues involved in the interaction.
Figure 2B:
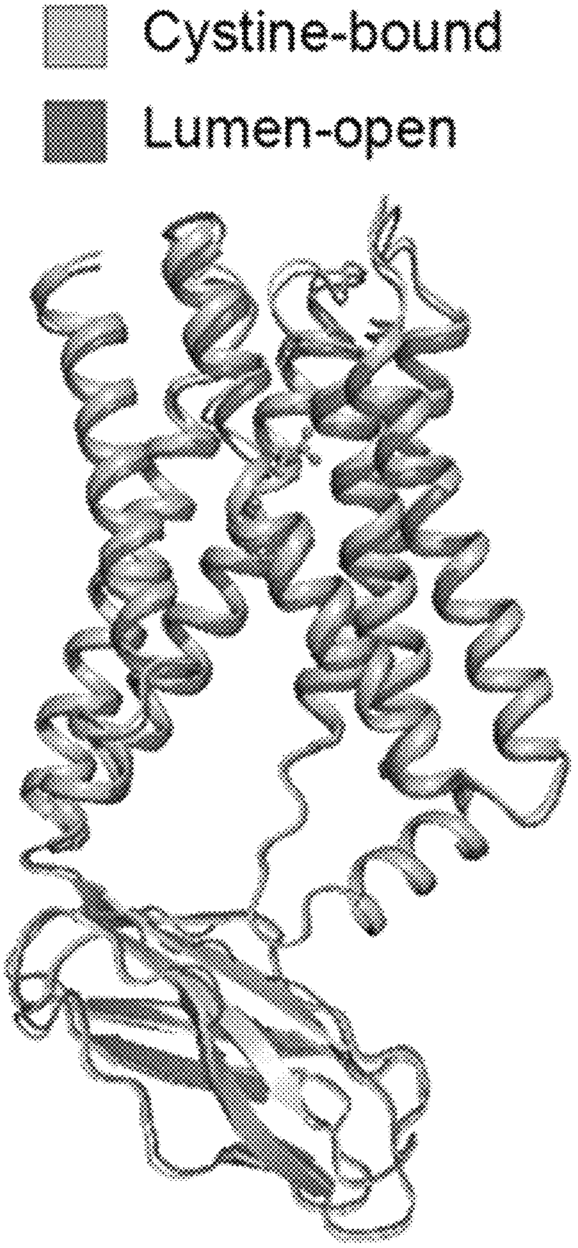
FIG. 2B shows a comparison of cryo-EM cysteine-bound (cyan) and lumen-open (blue) structures.

To gain insights into how Cystinosin specifically recognizes its substrate, cysteine, the cryo-EM structure of Cystinosin in the presence of cysteine was determined. The resulting structure resolved to 3.4 Å resolution, and an elongated extra density was found at the bottom part of the central cavity. This density was absent in the apo structures of Cystinosin, which were determined without the addition of cysteine, and the shape fits the molecular structure of cysteine (FIG. 2A). This density was attributed to cysteine. The structure of this cysteine-bound Cystinosin superimposes well onto that of the apo lumen-open state of Cystinosin (FIG. 2B), representing a substrate-bound, lumen-open state. The structure revealed that multiple cavity-lining residues interact with the amino acid moieties on both ends of cysteine (FIG. 2A). One amino acid moiety occupies a central region of the binding pocket and interacts with K273, K280, Y281, and D305, while the other amino acid moiety inserts into the bottom of the binding pocket and interacts with N166 and N301. W138 forms a hydrogen bond with D305, which stabilizes its conformation to interact with cysteine, and is in close range to cysteine. F142 and F170 are also in range to form hydrophobic interactions with cysteine around its disulfide bridge, in a similar interaction mode as that of other soluble cysteine-binding proteins (Bulut et al., 2012; Lu et al., 2014).

Figure 2C:
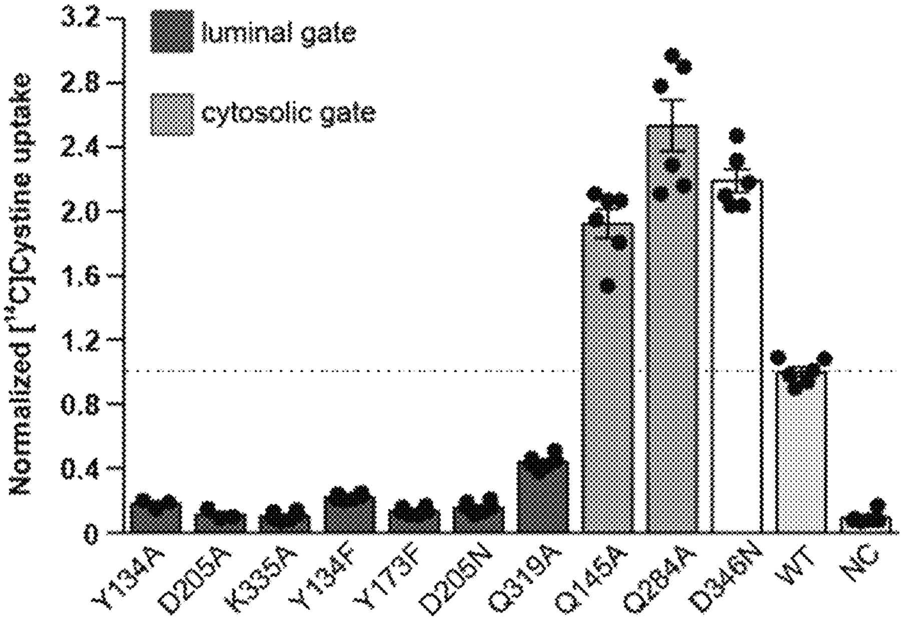
FIG. 2C shows cysteine uptake activities of Cystinosin mutants, normalized to wild type (dashed line) (mean±s.e.m.; n=6 independent experiments). WT, wild type; NC, negative control.
Figure 2D:
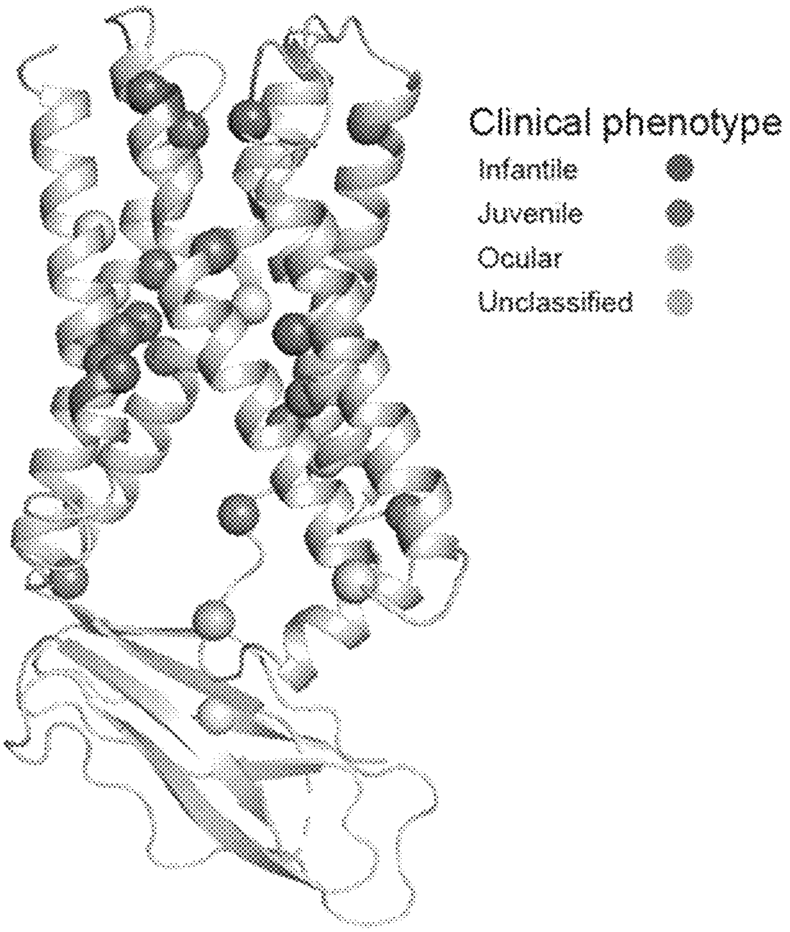
FIG. 2D shows missense mutations identified in cystinosis mapped onto the lumen-open structure of Cystinosin. Mutations are shown as spheres and colored on clinical phenotypes as indicated.

To probe the roles of these substrate binding pocket residues, mutagenesis studies were carried out. Mutating K273, K280, D305, W138, N166 and F142 abolished cysteine transport, while mutating Y281, N301 and F170 substantially reduced transport activity (FIG. 2C). These results show the important role of these residues in transport function, corroborating structural observations. Notably, K280 and D305 are clinically relevant as mutation of either residue causes cystinosis (FIG. 2D), further demonstrating their functional importance.

Compared to many other amino acid transporters that can transport multiple amino acids with similar properties, Cystinosin has a tight substrate selectivity for cysteine over all canonical amino acids. The Cystinosin structures reveal a narrow and elongated cavity that fits well with the shape of cysteine (FIG. 2A). Importantly, Cystinosin makes specific interactions with the amino and carboxyl groups on both ends of cysteine, providing a “molecular ruler” that dictates the selectivity for the dimeric cysteine over the monomeric canonical amino acids.

Luminal and Cytosolic Gates

Figure 3A:
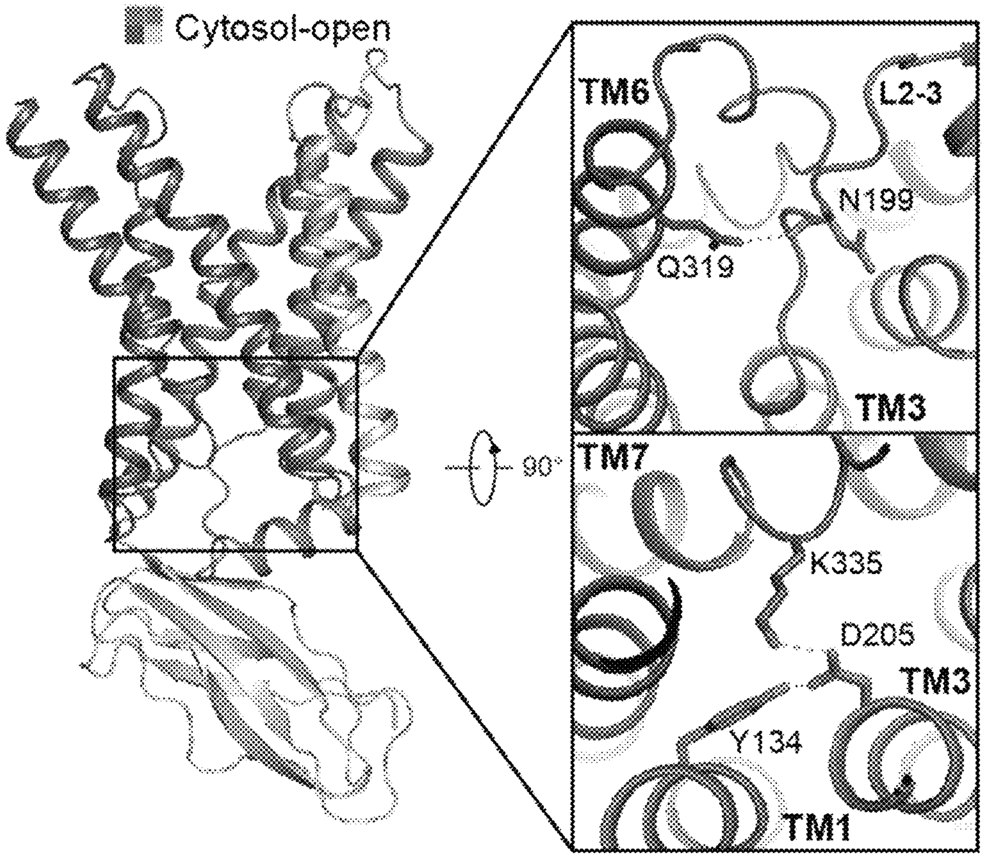
FIG. 3A shows the overall structure of cytosol-open Cystinosin with close-up views of the luminal gate. Residues involved in gate formation are shown as sticks.
Figure 3B:
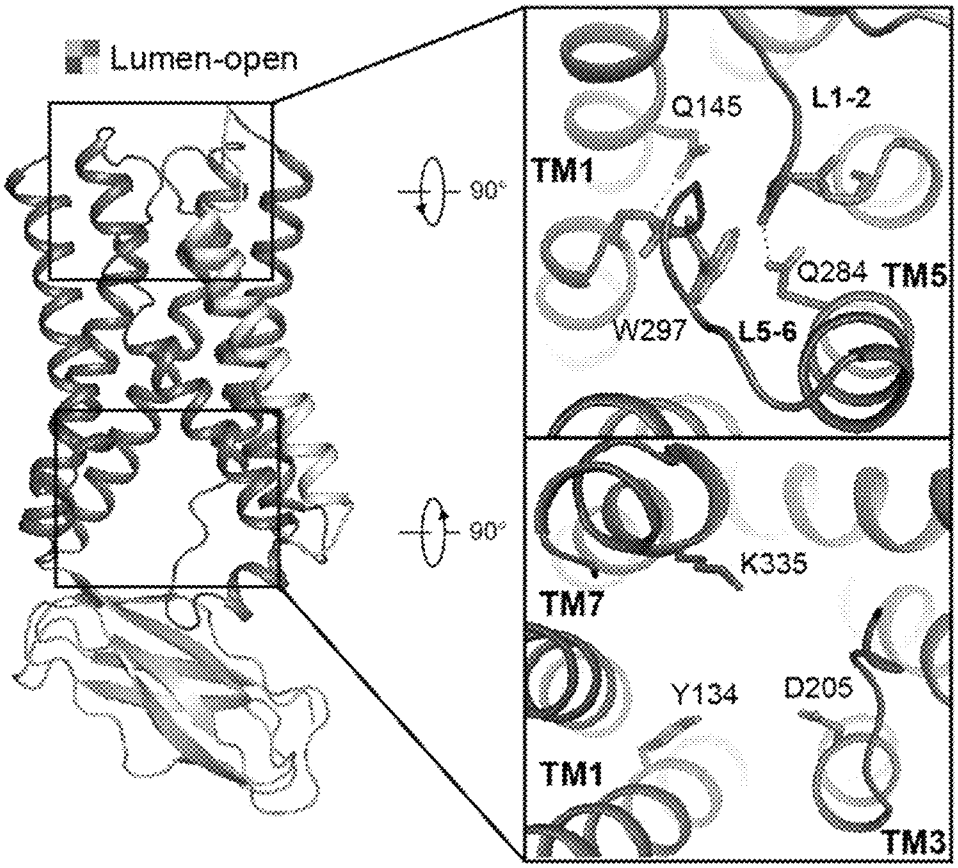
FIG. 3B shows the overall structure of lumen-open Cystinosin with close-up views of cytosolic (top) and luminal (bottom) gates. Residues involved in gate formation are shown as sticks. The hydrophilic interactions are indicated by gray dashes.

During the transport cycle, the luminal and cytosolic gates control the access of the substrate binding pocket to either side of the membrane and thus play central roles in the alternating transport mechanism. Comparing the structures of Cystinosin in cytosol-open (FIG. 3A) vs. lumen-open (FIG. 3B) conformations revealed key elements of the luminal and cytosolic gates. In the cytosol-open conformation, the central substrate translocation pathway is sealed from the lysosomal lumen by a luminal gate formed by an interaction network of residues, Y134, D205 and K335 (FIG. 3A). D205 on TM3 forms a salt bridge with K335 on TM7, which brings the luminal side of THB1 and THB2 in close proximity. In addition, Y134 interacts via hydrogen bonding with D205, which helps to stabilize its interaction with K335. These interactions are specific to the cytosol-open conformation and are absent in the lumen-open conformation (FIG. 3B). The formation of the luminal gate is associated with the repositioning L2-3. In association with the inward titling of TM2 and TM3 at the luminal side, L2-3 runs across the center of the mouth of the translocation pathway and shields the vestibule from the lysosomal lumen. In this conformation, L2-3 interacts with R114 on NTD and Q319 on TM6 from THB2, which may help stabilize the closed luminal gate.

Alanine substitution of Y134, D205 and K335 resulted in complete loss of cysteine transport activity (FIG. 3C), and the more conservative substitutions D205N or Y134F also abolished Cystinosin transport function, suggesting the importance of the interaction network of the luminal gate. In addition, the Q319A mutation substantially reduced cysteine uptake, pointing to an important role of residues that facilitate the closing of the luminal gate.

In the lumen-open conformation, the translocation pathway is sealed off from the cytosolic side by the cytosolic gate. The glutamine residues of the signature PQ motifs on both THBs are key in closing the cytosolic gate (FIG. 3B). Q145 of the first PQ motif forms a hydrogen bond with backbone amides on the cytosolic loop that connects TM5 and TM6 (L5-6). The bulky sidechain of W297 on L5-6 interacts with Q284 of the second PQ motif through amide-π stacking (FIG. 3B). Q284 is also in range to form a hydrogen bond with the backbone oxygen on the cytosolic loop L1-2. Thus, the interaction network mediated by Q145 and Q284 brings L1-2 on THB1 and L5-6 on THB2 in close proximity at the entrance of the central cavity, shielding the cavity from the cytosolic solvent. In addition, W297 on L5-6 inserts its indole ring into the central cavity, which helps occlude the translocation pathway.

Figure 3C:
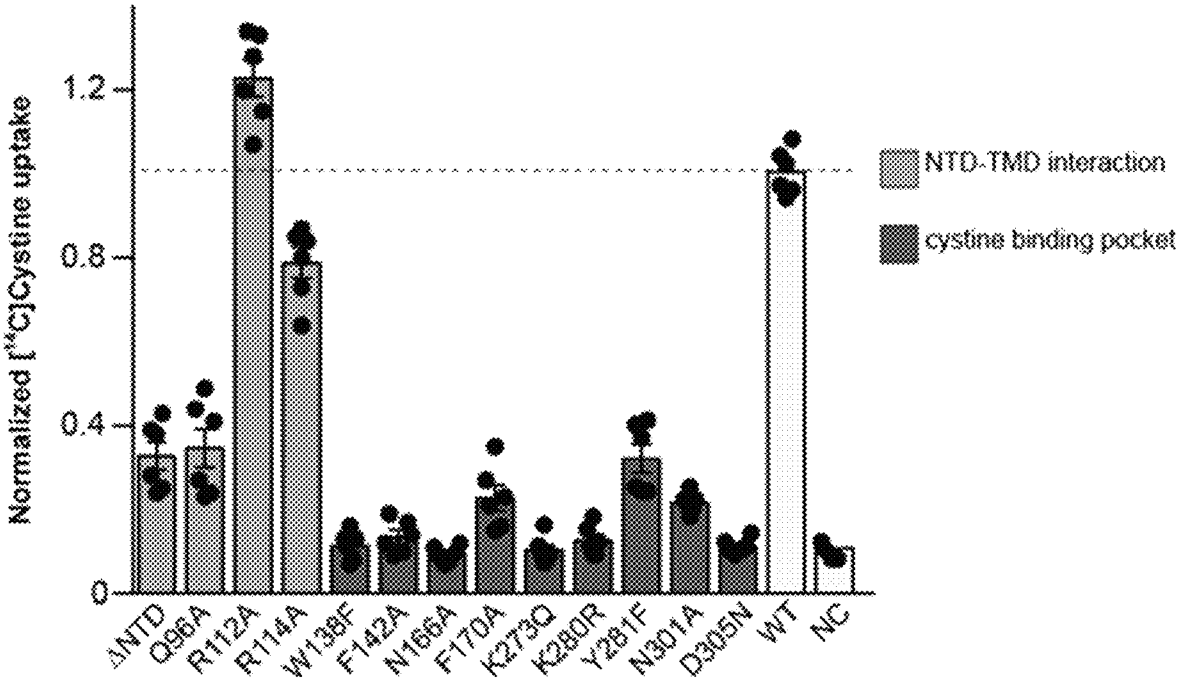
FIG. 3C shows cysteine uptake activities of Cystinosin with gate mutations or D346 mutation, normalized to wild type (dashed line) (mean±s.e.m.; n=3 or 6 independent experiments).
Figure 3D:
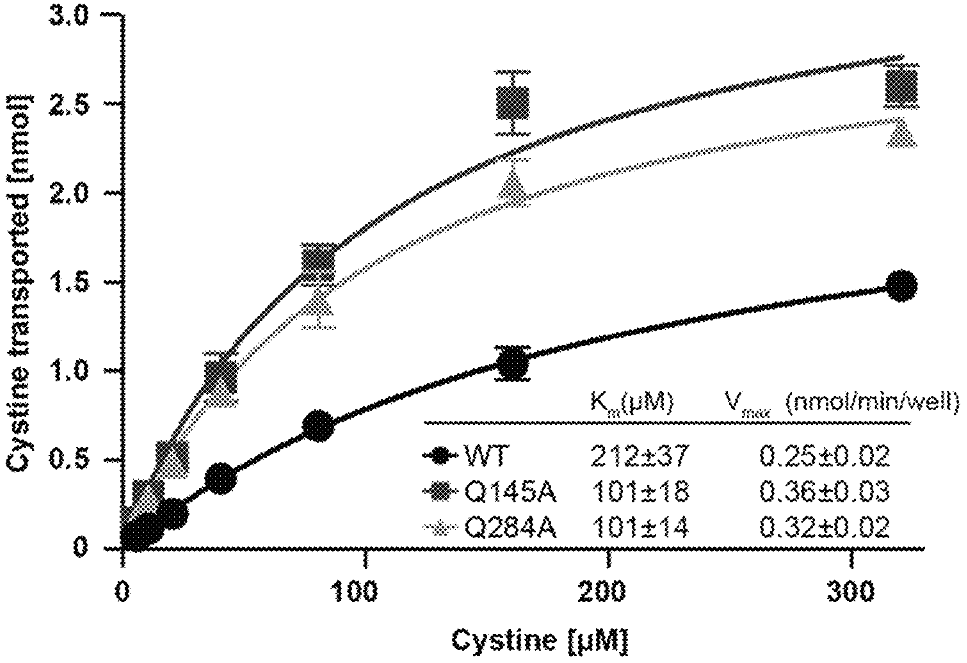
FIG. 3D shows saturation transport of wild type, Q145A and Q284A (mean±s.e.m.; n=3 independent experiments).

To probe the roles of the key residues that form the cytosolic gate, the effect of the alanine substitution on Q145 and Q284 was assayed. Both variants showed clearly enhanced cysteine uptake activity with a reduction in the Michaelis constant ($K_m$) and an increase in the maximum velocity ($V_{max}$) (FIG. 3D). These gain-of-function mutations reveal the important functional impact of weakening cytosolic gate formation by breaking the interactions mediated by Q145 or Q284. Intriguingly, this has the opposite effect to weakening the luminal gate formation (FIG. 3C).

The invention claimed is:

1. An anti-cystinosin epitope binding agent or conjugate thereof, comprising a heavy chain variable region ($V_H$) comprising:

(a) a CDR-H1 comprising the amino acid sequence set forth in SEQ ID NO: 1;

(b) a CDR-H2 comprising the amino acid sequence set forth in SEQ ID NO: 2; and (c) a CDR-H3 comprising the amino acid sequence set forth in SEQ ID NO: 3;

and a light chain variable region ($V_L$) comprising:

(d) a CDR-L1 comprising the amino acid sequence set forth in SEQ ID NO: 7;

(e) a CDR-L2 comprising the amino acid sequence set forth in SEQ ID NO: 8; and (f) a CDR-L3 comprising the amino acid sequence set forth in SEQ ID NO: 9.

2. The anti-cystinosin epitope binding agent or conjugate thereof of claim 1, wherein the $V_H$ comprises an amino acid sequence comprising at least 70% identity to the amino acid sequence set forth in SEQ ID NO: 13.

3. The anti-cystinosin epitope binding agent or conjugate thereof of claim 2, wherein the $V_L$ comprises an amino acid sequence comprising at least 70% identity to the amino acid sequence set forth in SEQ ID NO: 14.

4. The anti-cystinosin epitope binding agent or conjugate thereof of claim 1, wherein the epitope binding agent is an antibody or fragment thereof.

5. The anti-cystinosin epitope binding agent or conjugate thereof of claim 4, wherein the antibody or fragment thereof is selected from the group consisting of: a monoclonal antibody, an IgG, Fv, diabody, scFv, F(ab')2, and Fab.

6. The anti-cystinosin epitope binding agent or conjugate thereof, of claim 1, further comprising a detection molecule.

7. The anti-cystinosin epitope binding agent or conjugate thereof of claim 6, wherein the detection molecule comprises a fluorescent label, phosphorescent molecule, chemiluminescent molecule, chromophore, luminescent molecule, photoaffinity molecule, colored particle and/or ligands.

8. A kit comprising:

(a) the anti-cystinosin epitope binding agent or conjugate thereof of claim 1;

(b) reagents; and (c) instructions for use.

9. The anti-cystinosin epitope binding agent or conjugate thereof of claim 7, wherein the detection molecule comprises a biotin fluorescent dye, electrochemiluminescence dye, metal-chelate complex or label.

10. The anti-cystinosin epitope binding agent or conjugate thereof of claim 1, wherein the $V_H$ comprises an amino acid sequence comprising at least 70% identity to the amino acid sequence set forth in SEQ ID NO: 13, and the $V_L$ comprises an amino acid sequence comprising at least 70% identity to the amino acid sequence set forth in SEQ ID NO: 14.

11. The anti-cystinosin epitope binding agent or conjugate thereof of claim 1, wherein the $V_H$ comprises an amino acid sequence comprising at least 80% identity to the amino acid sequence set forth in SEQ ID NO: 13, and the $V_L$ comprises an amino acid sequence comprising at least 80% identity to the amino acid sequence set forth in SEQ ID NO: 14.

12. The anti-cystinosin epitope binding agent or conjugate thereof of claim 1, wherein the $V_H$ comprises an amino acid sequence comprising at least 90% identity to the amino acid sequence set forth in SEQ ID NO: 13, and the $V_L$ comprises an amino acid sequence comprising at least 90% identity to the amino acid sequence set forth in SEQ ID NO: 14.

13. The anti-cystinosin epitope binding agent or conjugate thereof of claim 1, wherein the $V_H$ comprises an amino acid sequence comprising at least 95% identity to the amino acid sequence set forth in SEQ ID NO: 13, and the $V_L$ comprises an amino acid sequence comprising at least 95% identity to the amino acid sequence set forth in SEQ ID NO: 14.

14. The anti-cystinosin epitope binding agent or conjugate thereof of claim 1, wherein the $V_H$ comprises an amino acid sequence comprising the amino acid sequence set forth in SEQ ID NO: 13, and the $V_L$ comprises an amino acid sequence comprising the amino acid sequence set forth in SEQ ID NO: 14.

15. The anti-cystinosin epitope binding agent or conjugate thereof of claim 14, which is an antibody or fragment thereof selected from the group consisting of: a monoclonal antibody, an IgG, Fv, diabody, scFv, F (ab')2, and Fab.

16. An anti-cystinosin epitope binding agent or conjugate thereof, comprising a heavy chain variable region ($V_H$) comprising:

(a) a CDR-H1 comprising an amino acid sequence having at least 90% identity to the amino acid sequence set forth in SEQ ID NO:1;

(b) a CDR-H2 comprising an amino acid sequence having at least 90% identity to the amino acid sequence set forth in SEQ ID NO:2; and (c) a CDR-H3 comprising an amino acid sequence having at least 90% identity to the amino acid sequence set forth in SEQ ID NO:3;

and a light chain variable region ($V_L$) comprising:

(d) a CDR-L1 comprising an amino acid sequence having at least 90% identity to the amino acid sequence set forth in SEQ ID NO:7;

(e) a CDR-L2 comprising an amino acid sequence having at least 85% identity to the amino acid sequence set forth in SEQ ID NO:8; and (f) a CDR-L3 comprising an amino acid sequence having at least 90% identity to the amino acid sequence set forth in SEQ ID NO:9, wherein the anti-cystinosin epitope binding agent or conjugate thereof specifically binds to a conformational epitope of the luminal domain of folded human cystinosin.

17. The anti-cystinosin epitope binding agent or conjugate thereof of claim 16, wherein the $V_H$ comprises an amino acid sequence comprising at least 95% identity to the amino acid sequence set forth in SEQ ID NO: 13, and the $V_L$ comprises an amino acid sequence comprising at least 95% identity to the amino acid sequence set forth in SEQ ID NO: 14.

18. The anti-cystinosin epitope binding agent or conjugate thereof of claim 16, wherein the $V_H$ comprises an amino acid sequence comprising at least 97% identity to the amino acid sequence set forth in SEQ ID NO: 13, and the $V_L$ comprises an amino acid sequence comprising at least 97% identity to the amino acid sequence set forth in SEQ ID NO: 14.

19. The anti-cystinosin epitope binding agent or conjugate thereof of claim 16, wherein the $V_H$ comprises an amino acid sequence comprising at least 99% identity to the amino acid sequence set forth in SEQ ID NO:13, and the $V_L$ comprises an amino acid sequence comprising at least 99% identity to the amino acid sequence set forth in SEQ ID NO: 14.

20. The anti-cystinosin epitope binding agent or conjugate thereof of claim 16, wherein (a) wherein any amino acid substitution present in CDR-H1 is a conservative amino acid substitution relative to SEQ ID NO:1;

(b) wherein any amino acid substitution present in CDR-H2 is a conservative amino acid substitution relative to SEQ ID NO:2;

(c) wherein any amino acid substitution present in CDR-H3 is a conservative amino acid substitution relative to SEQ ID NO:3;

(d) wherein any amino acid substitution present in CDR-L1 is a conservative amino acid substitution relative to SEQ ID NO:7;

(e) wherein any amino acid substitution present in CDR-L2 is a conservative amino acid substitution relative to SEQ ID NO:8; and (f) wherein any amino acid substitution present in CDR-L3 is a conservative amino acid substitution relative to SEQ ID NO:9.

* * * * *